US011545265B2

(12) United States Patent
Khine et al.

(10) Patent No.: US 11,545,265 B2
(45) Date of Patent: Jan. 3, 2023

(54) PREDICTIVE RESPIRATORY MONITOR AND SYSTEM

(71) Applicant: The Regents of the University of California, Oakland, CA (US)

(72) Inventors: Michelle Khine, Irvine, CA (US); Jonathan Pegan, Hillsboro, OR (US); Eugene Lee, Irvine, CA (US); Michael Chu, Irvine, CA (US); Francis Duhay, Irvine, CA (US); Mark Bachman, Oakland, CA (US); Joshua Kim, Oakland, CA (US); Sun-Jun Park, Oakland, CA (US)

(*) Notice: Subject to any disclaimer, the term of this patent is extended or adjusted under 35 U.S.C. 154(b) by 304 days.

(21) Appl. No.: 15/803,664

(22) Filed: Nov. 3, 2017

(65) Prior Publication Data
US 2018/0129786 A1 May 10, 2018

Related U.S. Application Data

(60) Provisional application No. 62/417,892, filed on Nov. 4, 2016.

(51) Int. Cl.
*G16H 50/20* (2018.01)
*G16H 10/60* (2018.01)
*G06N 20/00* (2019.01)

(52) U.S. Cl.
CPC ............ *G16H 50/20* (2018.01); *G06N 20/00* (2019.01); *G16H 10/60* (2018.01)

(58) Field of Classification Search
CPC .... G06F 19/3418; G16H 50/20; G16H 10/60; G06N 20/00
See application file for complete search history.

(56) References Cited

U.S. PATENT DOCUMENTS

| 7,382,247 B2 * | 6/2008 | Welch | G16H 40/63 340/539.12 |
| 2010/0234182 A1 * | 9/2010 | Hoffman | A61B 5/1125 482/8 |

(Continued)

FOREIGN PATENT DOCUMENTS

| WO | WO-2015085182 A1 * | 6/2015 | ........... H04L 67/125 |
| WO | WO 2015/179320 A1 | 11/2015 | |

(Continued)

OTHER PUBLICATIONS

Yan Wang, et al, Wearable and Highly Sensitive Graphene Strain Sensors for Human Motion Monitoring, Apr. 14, 2014, Advanced Functional Materials, vol. 24, pp. 4666-4670. (Year: 2014).*

(Continued)

*Primary Examiner* — Jonathan Durant
*Assistant Examiner* — Anne-Marie K Alderson
(74) *Attorney, Agent, or Firm* — Knobbe, Martens, Olson & Bear, LLP

(57) ABSTRACT

A mobile medical device for monitoring a respiratory condition in a subject, the medical device including: a sensor configured to be adhered to the skin of a patient, the sensor configured to yield a resistance signal that is modulated by movements of a chest of a patient during respiration; a sensor attachment module configured to receive the signal from the sensor and to output data to a mobile electronic device an indication of an adverse respiratory event. Also disclosed is a server for integrating data collected from a plurality of the mobile medical devices and a crowd-sourced respiration advisory system including a plurality of the mobile medical devices and a server for integrating data collected by the mobile medical devices.

15 Claims, 22 Drawing Sheets

(56) References Cited

U.S. PATENT DOCUMENTS

| | | | | |
|---|---|---|---|---|
| 2012/0037159 | A1* | 2/2012 | Mulqueeny | A61M 16/06 |
| | | | | 128/204.23 |
| 2012/0071743 | A1* | 3/2012 | Todorov | G06F 19/3481 |
| | | | | 600/372 |
| 2017/0023509 | A1* | 1/2017 | Kim | G01N 27/126 |
| 2017/0364653 | A1* | 12/2017 | Wong | G16H 40/67 |
| 2018/0103899 | A1* | 4/2018 | Cahan | A61B 5/6862 |

FOREIGN PATENT DOCUMENTS

| | | | | |
|---|---|---|---|---|
| WO | WO-2015179320 | A1 * | 11/2015 | G01B 7/20 |
| WO | WO-2017020111 | A1 * | 2/2017 | A41D 1/002 |
| WO | WO-2017032873 | A2 * | 3/2017 | A61B 5/7275 |

OTHER PUBLICATIONS

Pegan, Jonathan D. et al., Skin-mountable stretch sensor for wearable health monitoring, published Sep. 26, 2016, Nanoscale 8, pp. 17295-17303 (Year: 2016).*

Asthma and Allergen Society 1995 "Cost of Asthma on Society" on the World-Wide-Web at aafa.org/page/cost-of-asthma-on-society.aspx., downloaded Apr. 26, 2018.

Ausman et al. 2000 "Organic Solvent Dispersions of Single-Walled Carbon Nanotubes: Toward Solutions of Pristine Nanotubes" *J Phys Chem B* 104: 8911-8915.

Byun I. et al. 2013 "Transfer of thin Au films to polydimethylsiloxane (PDMS) with reliable bonding using (3-mercaptopropyl)trimethoxysilane (MPTMS) as a molecular adhesive" *J Micromech Microeng* 23(8): 1-10.

D'Amato et al. 2010 "Urban Air Pollution and Climate Change as Environmental Risk Factors of Respiratory Allergy: An Update" J Invest Allerg Clin 20(2): 95-102.

Dillon, A. (2003) User Interface Design. MacMillan Encyclopedia of Cognitive Science, vol. 4, London: MacMillan, 453-458.

Drotar D and Bonner MS 2009 "Influences on adherence to pediatric asthma treatment: a review of correlates and predictors" *J Dev Behav Pediatr.* 30(6): 574-582.

Dumonteil et al. 2006 "Dispersion of carbon nanotubes using organic solvents" *J Nanosci Nanotechnol* 6(5): 1315-1318.

Hammer SC, et al. 2008 "Actual asthma control in a paediatric outpatient clinic population: do patients perceive their actual level of control?" *Pediatr Allergy Immunol.* 19 (7): 626-633.

Hmeidi et al. 2017 "Tidal breathing parameters measured using structured light plethysmography in healthy children and those with asthma before and after bronchodilator" *Physiol Rep.* 5(5): e13168 (in 12 pages).

Kamps Awa et al. 2001 "Peak flow diaries in childhood asthma are unreliable" *Thorax* 56(3):180-182.

Lambauch, R.J. and Kipen, H.M. 2012 "Respiratory health effects of air pollution: Update on biomass smoke and traffic pollution" *J Allergy Clin Immmunol* 129(1): 3-13.

Li et al. 2012 "Dispersion of Carbon Nanotubes in Organic Solvents Initiated by Hydrogen Bonding Interactions" *AIChE Journal* 58: 2997-3002.

Limpomi, D.J. et al. 2011 "Skin-like pressure and strain sensors based on transparent elastic films of carbon nanotubes" Nature Nanotech 6: 788-792.

Lipworth, B.J., 1999 "Systemic Adverse Effects of Inhaled Corticosteroid Therapy—A Systematic Review and Meta-analysis" *Arch Intern Med.* 159(9): 941-955.

National Heart Lung and Blood Institute, 2007 What is Asthma? NIH Medline Plus, on the internet at: medlineplus.gov/magazine/issues/fall07/articles/fall07pg14.html.

National Heart, Lung, and Blood Institute (NHLBI), 2014 "Living With Asthma", on the World-Wide-Web at nhlbi.nih.gov/health-topics/asthma.

Pegan, J.D., Zhang, J., Chu, M., Nguyen, T., Park, S.J., Paul, A., Kim, J., Bachman, M., Khine, M. Skin-Mountable Stretch Sensor for Wearable Health Monitoring, Nanoscale, 2016,8, 17295-17303.

Roman, D.H, Conlee, J.D., The Digital Revolution Comes to US Healthcare, Goldman Sachs Equite Report Jun. 29, 2015.

Rosenthal, E. "The Soaring Cost of a Simple Breath", New York Times, Oct. 12, 2013.

Vasbinder E, Dahhan N, Wolf B, Zoer J, Blankman E, Bosman D, van Dijk L, van den Bernt P: The association of ethnicity with electronically measured adherence to inhaled corticosteroids in children. Eur J Clin Pharmacol. 2012, 69 (3): 683-690.

Vasbinder, E., Janssens, HM, e-Monitoring of Asthma Therapy to Improve Compliance in children using a real-time medication monitoring system (RTMM): the e-MATIC study protocol, BMC Medical Informatics and Decision Making, 2013, 13:38.

World Health Organization 2007 "Global surveillance, prevention and control of chronic respiratory diseases: a comprehensive approach".

Yoos HL, Kitzman H, McMullen A, Henderson C, Sidora K. Symptom monitoring in childhood asthma: a randomized clinical trial comparing peak expiratory flow rate with symptom monitoring. Ann Allergy Asthma Immunol Mar. 2002;88(3):283-291.

Zhanf, Z., Zheng, J., Wu, Hao, Wang, W., Wang, B., Liu, H., Development of a Respiratory Inductive Plethysmography Module Supporting Multiple Sensors for Wearable Systems Sensors 2012, 12, 13167-13184.

\* cited by examiner

Before Shrinking

After Shrinking

PREDICTIVE RESPIRATORY MONITOR AND SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application is directed to a predictive respiratory monitor, and systems and methods implemented in and using the same.

Description of the Related Art

More than 24 million people suffer from asthma in the US alone. Worldwide, 250,000 people die prematurely per year due to asthma attacks. Almost all of these deaths are preventable. Currently, however, there is no way to automatically detect, much less predict the onset of an asthmatic event.

Air pollution contributes to the large global burden of respiratory and allergic diseases including asthma, chronic obstructive pulmonary disease, pneumonia and possibly tuberculosis (Lambauch and Kipen 2012 J *Allergy Clin Immmunol* 129(1): 3-13). Worldwide increases in rates of asthma and COPD over the past several decades have motivated intensive investigation of the role of environmental factors, including air pollution, in their causation. Recent research also suggests that air pollution contributes to the substantial worldwide burden of disease from acute lower respiratory infections and possibly tuberculosis. While the health effects of air pollution have been an international public health concern since at least the 1950's, recent research has heightened the focus on two broad sources of air pollution: biomass fuels (BMF) and motor vehicles. Understanding of the health effects of BMF and traffic-related air pollution (TRAP) has lagged behind that of ambient air pollution, at least in part due to challenges in estimating highly-variable individual exposure from these widespread, but very localized, air pollution sources.

Air pollution is only one of many environmental (non-genetic) factors for which a causative role in exacerbation or incidence of complex respiratory diseases has been suggested. Studies with individual-level analyses that control for potential confounding have demonstrated associations between air pollutants, including TRAP, and asthma exacerbation, as well as possible links to increased asthma incidence. Additional evidence suggests that exposure to TRAP is correlated with the rising rates of allergic respiratory disease (D'Amato et al. 2010 *J Invest Allerg Clin* 20(2): 95-102). Although tobacco smoke is a dominant cause of COPD worldwide, BMF smoke is now recognized as a major cause of COPD, especially among women in less developed countries.

Peak flow meter testing is currently the gold standard for asthma monitoring. However, peak flow meters have a number of drawbacks, including that the test: is taken discrete, for example yielding data 2-3 times a day; is highly variable, for example with sitting and standing yielding different results; is difficult to control, for example consisting of getting the patient to exhale 'maximally,' such that the test is not recommended for whole classes of patients, such as children under 12; is implemented with manual tracking; and it lacks automated trend and onset detection.

Some sophisticated monitors exist for non-invasive monitoring of respiration, but providing advances in this technology would be advantageous.

SUMMARY OF THE INVENTION

As discussed below, a stretch sensor can be provided for respiratory monitoring. The stretch sensor can be combined with machine learning algorithms to detect signatures of pulmonary difficulties. The stretch sensor alone or with machine learning can be combined with a crowd sourcing application to alert others in the area who may be vulnerable to suffering from pulmonary issues. Because asthma attacks can be triggered by allergens in the environment, the crowd sourcing application would alert persons monitoring the output thereof not to go to that area.

In one embodiment, a system for monitoring respiratory conditions is provided. The system includes a sensor and a data processing system. The sensor can be configured to be adhered to the skin of a patient. The sensor can be configured to yield a detectable signal that is modulated by movements of a chest of a patient during respiration. The detectable signal can be resistance in one embodiment. The data processing system is configured to receive the signal from the sensor and to output to a user an indication of an adverse respiratory event.

The system described above can be configured in one implementation to indicate the onset of an asthmatic event.

In another embodiment, a sensor is provided that can be used in a respiratory event detection system. The sensor can include a means to be secured temporarily to the skin of the user. The sensor can comprise variable resistance in response to patient respiration.

The foregoing embodiments can employ a sensor that is configured to stretch and when stretched to yield a modulated or changed measurable value, such as resistance.

In various embodiments, machine learning is employed to allow for or improve the detection of a respiratory event such as the on-set of an asthma attack or an asthmatic event.

An advisory system can be provided in one embodiment. The system includes any of the sensors disclosed herein. The sensors may be coupled with a processor that receives output from the sensor and that determines a useful output such as the fact of the on-set of a detectable respiratory event, the location and of such on-set, the time of such on-set, the user experiencing the event. The advisory system can provide that at least one other sensor can be coupled with the same or a different processor to determine the fact of an on-set of a detectable respiratory event, the location and of such on-set, and the time of such on-set as well as the identify of another user experiencing the event. The advisory system can provide one or more sensor(s), one or more processors, and one or more user output devices. The system can include geographical location detection technology, such as global positioning system components. The user output devices can include a computer device for generating a report. The computer device can include a computer connected to a network such as the Internet, a smart phone, table computer, or the like. The user output device can include a printer or other means for generating a report. A report that can be output can include a list of locations that are observed to be associated with the on-set of respiratory events for one or more users. The report can be graphical, such as including a map. The locations can be determined using GPS components or can rely on other technology and user input as to location.

The systems described herein can include a database that can be remotely stored and accessed by a plurality of user-associated processors or computer devices, e.g., a cloud based system.

Some embodiments relate to a mobile medical device for monitoring a respiratory condition in a subject, the medical device including:

a sensor configured to be adhered to the skin of a patient, the sensor configured to yield a resistance signal that is modulated by movements of a chest of a patient during respiration;

a sensor attachment module (SAM) configured to receive the signal from the sensor and to output data to a mobile electronic device an indication of an adverse respiratory event.

In some embodiments, the sensor comprises a stretch sensor.

In some embodiments, a detectable resistance of the sensor is configured to change upon stretching of the sensor.

In some embodiments, the sensor is mounted on or integrated into an article of clothing.

In some embodiments, the article of clothing is a belt.

In some embodiments, the mobile electronic device is selected form the group consisting of a smartphone, a desktop computer, a laptop computer, a netbook, a tablet computer, a smartwatch, an augmented reality wear, a PDA (personal digital assistants), a server, a digital camera, an e-book reader, a video game platform, a television set-top box (or simply a television with computing capability), a kiosk, and a combination thereof.

In some embodiments, the mobile electronic device is configured to automatically collect data and to transmit data to a server when a predetermined event-based condition is met.

In some embodiments, the mobile electronic device comprises a crowd sourcing application configured to receive data from the sensor attachment module, to transmit data to a server and to receive data from the server.

In some embodiments, the crowd sourcing application is configured to permit a user to manually tag an event or to enter descriptive data regarding an event.

Some embodiments relate to a lung function apparatus comprising:

a sensor configured to be adhered to the skin of a patient, the sensor configured to yield a resistance signal that is modulated by movements of a chest of the subject during respiration; and a sensor attachment module (SAM) configured to receive the signal from the sensor and to output data indicative of lung function to a display.

Some embodiments relate to a server for integrating data collected by a plurality of mobile medical devices according to claim 1, the server including:

a receiver configured to receive data transmitted from the plurality of mobile medical devices, the received data being collected by sensors of the plurality of mobile electronic devices;

an analytic engine configured to integrate data received from the plurality of mobile medical devices to create or update a map indicating respiratory condition information in connection with a plurality of users; and a transmitter configured to transmit the map to the plurality of mobile medical devices of the plurality of users, wherein the map indicates a respiratory condition to the plurality of users of the mobile medical devices.

In some embodiments, the map is a heat map.

In some embodiments, the server comprises a machine learning module to detect an adverse regional respiratory event.

In some embodiments, the machine learning module is configured to detect an asthmatic event.

In some embodiments, the server is configured to: train a respiratory distress detection model using machine learning techniques and one or more sets of training data, automatically detect an instance of suspected respiratory distress by an entity using the respiratory distress detection model, and updating the respiratory distress detection model using at least a portion of the feedback data and machine learning techniques for use in detecting a second instance of suspected respiratory distress.

In some embodiments, the server is further configured to analyze the data collected from the mobile electronic devices to determine a further event or a next likely scenario.

Some embodiments relate to a crowd-sourced respiration advisory system including:

a plurality of mobile medical devices as disclosed herein; and a server for integrating data collected by mobile medical devices according to claim 1 of a plurality of users, the server including:

a receiver configured to receive data transmitted from the mobile medical devices of the plurality of users, the received data being collected by a sensor of the mobile electronic device;

an analytic engine configured to integrate data received from the mobile medical devices of the plurality of users to create or update a map indicating respiratory condition information in connection with the plurality of users; and a transmitter configured to transmit the map to the mobile medical devices of the plurality of users, wherein the map indicates a respiratory condition of the plurality of users of the mobile medical devices.

In some embodiments, the respiration advisory system further comprises a database, the server being in communication with the database to store the indication of the adverse respiratory event.

In some embodiments, the respiration advisory system is configured to provide to one or more user display devices a report indicating a geographic location of one or more adverse respiratory events.

In some embodiments, the respiration advisory system is configured to provide to one or more user display devices a map showing a geographic location of one or more adverse respiratory events.

Some embodiments relate to a method of assessing lung function or a method of monitoring a respiratory therapy in a subject comprising:

placing a mobile medical device as disclosed herein in communication with the chest or abdomen of the subject, and utilizing data output from the mobile medical device to assess lung function and/or to determine if the respiratory therapy is being carried out effectively.

BRIEF DESCRIPTION OF THE DRAWINGS

A more complete appreciation of the subject matter of this application and the various advantages thereof can be realized by reference to the following detailed description, in which reference is made to the accompanying drawings in which.

More detailed descriptions of various embodiments of components for predictive respiration monitors to detect respiratory conditions and to provide alerts as to adverse conditions are set forth below.

DETAILED DESCRIPTION OF THE PREFERRED EMBODIMENT

Flexible sensor apparatuses that can detect respiration are discussed below. These devices can be configured, e.g., by a software application described below, for measuring lung volume as well as breathing rate. Changes in 'normal' breathing, e.g., caused by an asthma attack or other breathing impairment, can be detected by monitoring normal breathing. For example, monitoring can be frequent throughout a day or a relevant period. Monitoring can be continuous throughout a day or relevant period in some embodiments.

In some configurations, predictive analytics can be incorporated to detect abnormal breathing, such as wheezing, cessation of breath, shallow breathing, rapid breathing, or any combination of these or other abnormal breathing patterns.

In some configurations the monitor, system or method detects abnormal breathing and thereafter sets off an alarm or an alert. In some configurations abnormal breathing sets off an alert to a remote monitoring device. Examples of remote monitoring devices include a cell phone or smart phone or other computer system or a monitoring station.

In one implementation, patients can join a data community. The data community can be configured to advise other members of the community of a condition potentially relevant to such other members. For example, a smart phone or a dedicated monitor with global positioning system (GPS) hardware can provide the specific location where abnormal breathing occurred, e.g., where an asthma attack occurred. The smart phone or dedicated monitor can provide details about the abnormal breathing, e.g., asthma attack and the location as an alarm that can be register on a graphical device such as a map. This device allows other members of the community with asthma or other respiratory conditions who may be nearby to be informed of areas with poor air quality or other conditions that correspond to high-incidences of abnormal breathing in the community. This information can serve as a warning to avoid the area. The alerts and other patient data can be stored in the cloud or other remote database such that longitudinal monitoring of patient and/or environmental condition can be assessed.

Respiration Monitoring System

Figure 1:
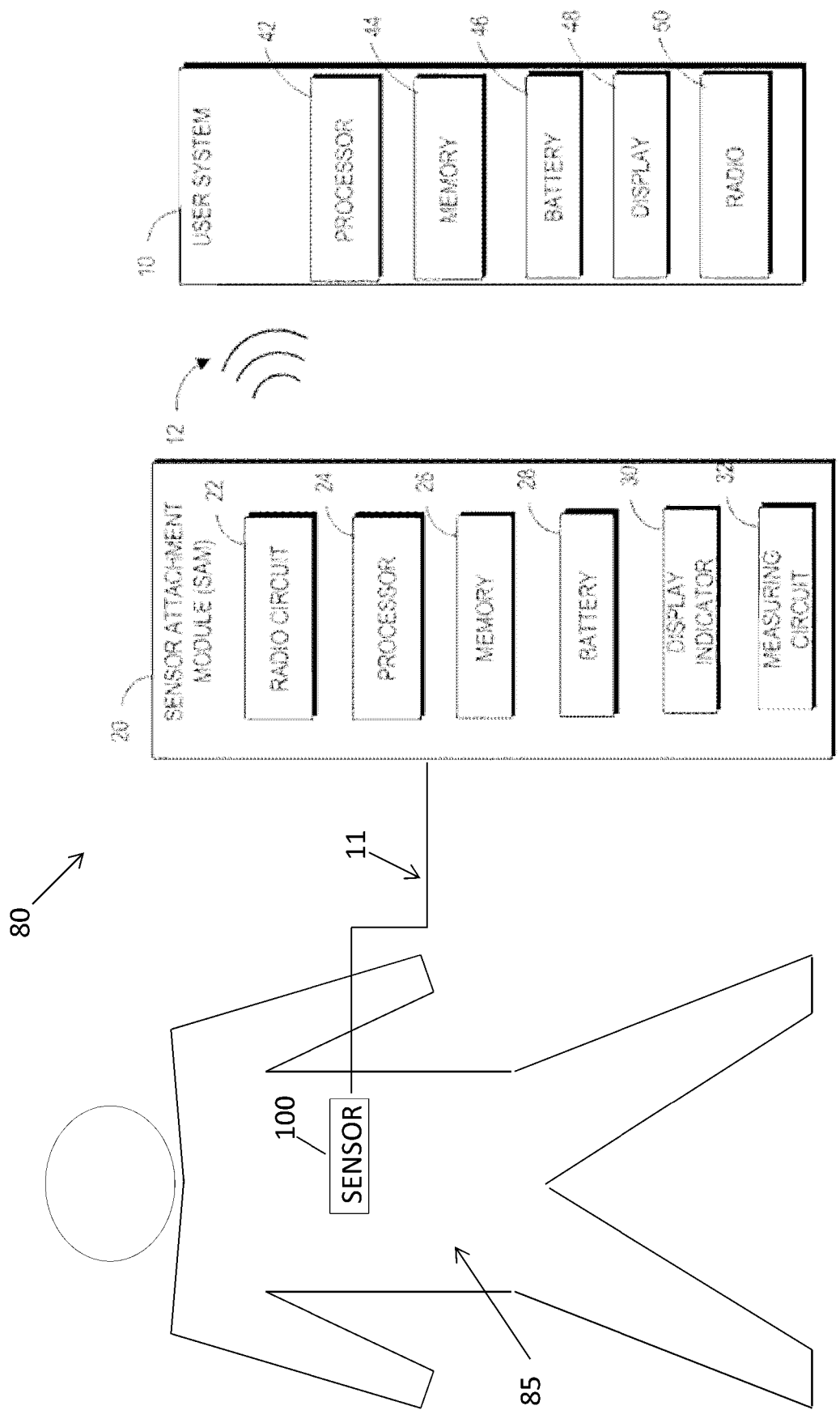
FIG. 1 shows a respiration monitoring system that includes a disposable patient interface and a strain sensor.
Figure 2:
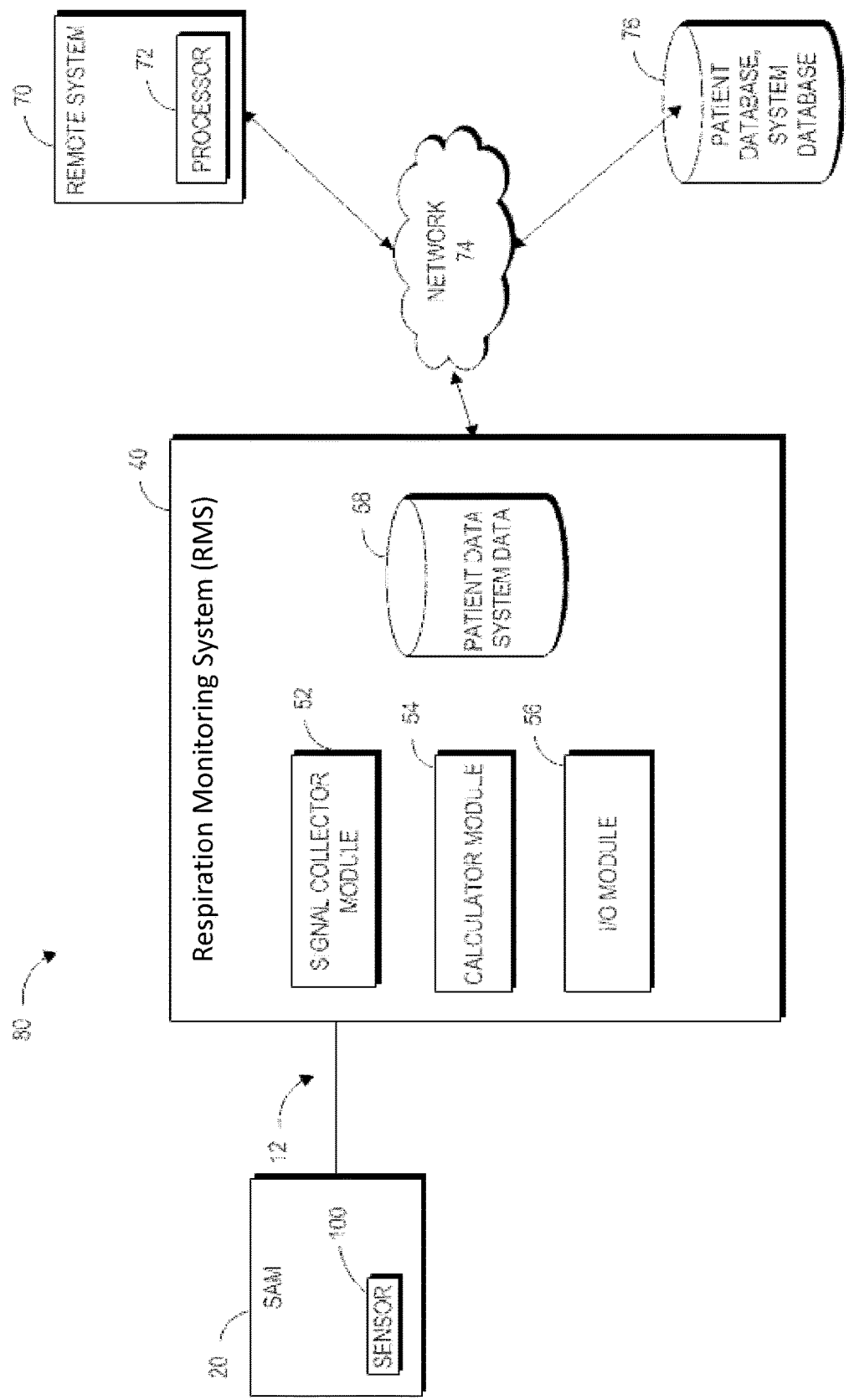
FIG. 2 shows a monitoring system including a wearable sensor, a sensor attachment module (SAM) and a respiration monitoring system (RMS).

FIGS. 1 and 2 show embodiments of a system 80 for monitoring respiration in a subject or a patient. The system 80 can includes as one subcomponent a patient coupled portion 2 to be placed on the patient for a period of time from hours to days. The patient coupled portion 2 includes in one embodiment a sensor apparatus 100 and a sensor attachment module 20. The sensor apparatus 100 is adapted to be coupled directly to a patient, e.g., to the abdomen. When so coupled, the sensor apparatus is conformal to the abdomen and is able to sense movements of the surface of the abdomen and of respiration by the patient. The sensor apparatus 100 can be integrated into a flexible interface that include a first side having an adhesive disposed thereon for connecting to the skin and a second side that is exposed.

The flexible interface can have a first end and a second end. The sensor apparatus 100 can reside at or in the first end. The integration of the sensor apparatus 100 into the flexible interface can include disposing the sensor apparatus on or adjacent to a lower surface of the flexible interface. In one embodiment, the flexible interface includes a thin and flexible fabric or plastic strip and a layer of adhesive and the sensor apparatus 100 is disposed on the lower surface of the flexible interface between the strip and the adhesive. In another embodiment, a portion of the sensor apparatus 100 is coupled with the fabric or plastic strip but a portion that is configured to be sensitive to strain is only indirectly coupled with the fabric to prevent the movement of the strain sensitive portion from being constrained. In this way, the strain sensitive portion of the sensor apparatus 100 is isolated from and prevented from being stiffened by the flexible interface. In other embodiments, where the flexible interface does not affect stiffen the strain sensitive portion of the sensor apparatus 100, the sensor apparatus can be disposed within the thickness of the flexible interface, e.g., spaced from both the lower and the upper surface of the fabric or strip portion.

The sensor attachment module 20 can be disposed at the second end of the flexible interface. In one embodiment, the sensor attachment module 20 is configured as a reusable component and the sensor apparatus 100 and the flexible interface 4 are configured as disposable components. The sensor attachment module 20 has a housing that encloses electronic components discussed below that receive and process the signals from the sensor apparatus 100. This allows the patient to remove the patient coupled portion for certain activities, such as bathing or swimming if some portions of the system 80 are not water poof. To re-connect the system 80, the patient couples another flexible interface with his or her abdomen and then makes a connection between the sensor and the sensor attachment module 20.

By reducing the connection between the sensor attachment module 20 and the flexible interface some mechanical isolation is provided between these components. This is advantageous in that the sensor apparatus 100 in certain embodiments includes a strain gauge which senses motion when under a strain. As such, motion and forces applied by the sensor attachment module 20 to the interface portion are prevented from introducing a significant source of error in the strain gauge readings. Also, most of the mass of the patient coupled portion is located in the sensor attachment module 20. By isolating this structure from the flexible interface, which is adhered to and conformal with the patient, comfort of the system is increased. Increasing patient comfort will enhance compliance with a monitoring regime.

An electrical connection 11 is provided between the sensor apparatus 100 and the sensor attachment module 20. The electrical connection 11 includes electrical traces that can have any suitable configuration. In some embodiments, the electrical connection 11 comprises one or more stretchable interconnect device. The traces can be directly integrated into to fabric or plastic portion of the flexible interface or can be disposed in another component, such as a flex cable as discussed below in connection with FIG. 16.

The flexible interface is elongate between the first end and the second end, extending along a longitudinal axis between the ends. In one approach, the flexible interface is connected to the patient's abdomen transverse to the mid-plane of the body.

Figure 5:
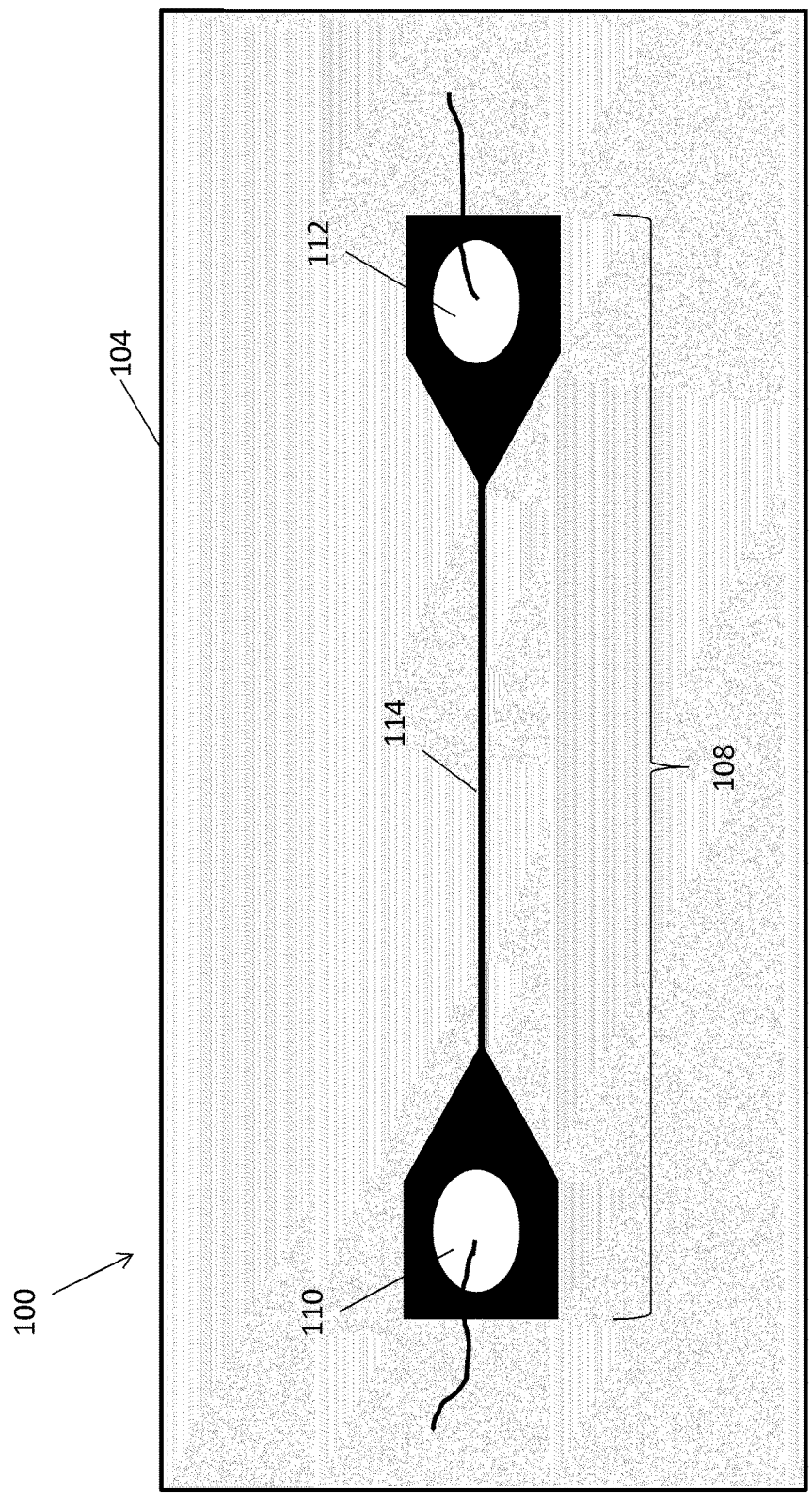
FIG. 5 depicts a wrinkled metal film strain gauge.

As discussed above, the system 80 includes the sensor apparatus 100 described more in detail with respect to one embodiment in FIG. 5 that is well suited for a wide range of strain applications, including high strain applications. These characteristics make the sensor apparatus 100 well adapted for coupling with a patient and with the sensor attachment module 20. The sensor attachment module 20 is coupled by a flexible, moveable medium, e.g., the flexible interface to be worn close to the chest.

Sensor Attachment Module

An embodiment of a sensor attachment module 20 is illustrated in FIG. 1. The sensor attachment module 20 can activate the sensor 100 and process signals received from the sensor 100. Activation of the sensor 100 can refer to measurement of a change in resistance of the sensor 100 using the measuring circuit 32. In some embodiments, the measuring circuit 32 includes a bridge circuit or any other circuit used for measuring a change in resistance in a strain gauge. The processor 24 can activate the measuring circuit 32 to sample the change in resistance over a period of time. The sampling frequency can be predetermined or dynamically change depending on patient data or a patient health event. For example, when the mother is having respiratory distress, the system 80 may determine to increase sampling frequency. In the alternative, in some embodiments, if there are no changes in the patient, the system 80 may reduce sampling frequency to conserve an onboard battery 28. In one embodiment, the sampling frequency is 10 Hz.

The sensor attachment module 20 may also include a radio circuit 22 for transmitting data to a respiration monitoring system (RMS) over a link 12. In an embodiment, the RMS 40 receives the transmitted data via the user system 10. The link 12 may be wired or wireless. In some embodiments, the radio circuit 22 includes electronics such as an antenna for transmitting data using the Bluetooth protocol. Other transmission protocols, such as NFC, WiFi, or the like can also be used to transmit data from the sensor attachment module to the RMS. Transmitting data can be taxing on the battery 28 of the sensor attachment module. Accordingly, in some embodiments, the processor 24 determines when to transmit data to the user system 10. For example, the processor 24 can transmit data in response to a signal received from the user system 10 requesting transmission of data from the patient. The processor 24 can also process the received signal from the sensor 100 locally to determine whether the sensor data 100 needs to be transmitted to the RMS for further processing. Local processing may include comparing one or more characteristics of the signal with a stored threshold. The processor 24 can also be programmed to determine transmission of data based on a time of day or a pre-determined time interval. The signal data from the sensor 100 can be stored in the memory 26. In some embodiments, the transmitted data from memory 26 can be cleared to conserve space for storing additional data from continuous monitoring. In some embodiments, the system 80 provides a continuous 24 hour monitoring of the patient. Also, the size, shape, and weight of the sensor attachment module 20 may be constrained by concerns relating to long term wear-ability. Thus, in some embodiments, it may be advantageous to conserve battery power because a larger battery may not be feasible. In one embodiment, the sensor attachment module 20 is flexible.

The processor 24 can be programmed to determine whether the sensor 100 is properly attached to the sensor attachment module. In some embodiments, the sensor 100 may be disposable, while at least some portions of the sensor attachment module 20 may be reusable. Accordingly, a patient may be required to self-attach the sensor 100 to the sensor attachment module 20. Thus, in some embodiments, the sensor attachment module 20 can include a display indicator 30 for informing the patient that the sensor 100 is properly attached with the sensor attachment module 20. The display indicator 30 can include an LED or an LCD display.

Patient Monitoring System

The transmitted signals from the sensor attachment module 20 are received by the radio communication module 50 of the patient monitoring system (40). In general, the user system 10 and remote system 70 can include any type of computing device capable of executing one or more applications and/or accessing network resources. For example, the user system 10 and the remote system 70 can be desktops, laptops, netbooks, tablet computers, smartphones, smartwatches, augmented reality wear, PDAs (personal digital assistants), servers, e-book readers, video game platforms, television set-top boxes (or simply a television with computing capability), a kiosk, combinations of the same, or the like. The user system 10 and the remote system 70 can include software and/or hardware for accessing the PMS system 40, such as a browser or other client software.

An embodiment of the user system 10 including a block diagram of its hardware modules is illustrated in FIG. 1. For example, the user system 10 can include a hardware processor 42, a memory unit 44, a radio communications module 50, and a battery 46. In some embodiments, the user system 10 can also include a user interface display 48 for displaying results of monitoring and/or receiving input from a user.

FIG. 2 illustrates an embodiment of a respiration monitoring system (RMS) 40. The RMS 40 can be implemented in computer hardware and/or software. The RMS 40 can execute on one or more computing devices, such as one or more physical server computers, including for example, user system 10 and remote system 70. In implementations where the RMS 40 is implemented on multiple servers, these servers can be co-located or can be geographically separate (such as in separate data centers). In addition, the RMS 40 can be implemented in one or more virtual machines that execute on a physical server or group of servers. Further, the RMS 40 can be hosted in a cloud computing environment, such as in the Amazon Web Services (AWS) Elastic Compute Cloud (EC2) or the Microsoft® Windows® Azure Platform. The RMS 40 can also be integrated with SAM 20 or user system 10 through software or hardware plug-in or an API (application programming interface). In some embodiments, some or all of the modules of the RMS 40 may be implement by a user system 10 or a remote system 70, or a combination of both. For instance, the user system 10 may implement the I/O module 56, while the rest of the modules are implemented remotely on the remote system 70 running on a server. In other embodiments, a plugin to the RMS 40 may be installed on to a third party tool.

The RMS 40 includes a signal collector module 52 for receiving signals and performing initial processing. Initial processing may include reducing noise from the received signal. The RMS 40 can also include an I/O module 56 that can generate a user interface for displaying results. The user interface can be displayed on the user system 10. The user interface can also include controls that can enable users to input data. For example, a patient can enter input data using the user system 10 including the generated user interface from the I/O module. The user interface can also display trends or calendar of characteristics related to a respiratory condition. Characteristics can correspond to a number or frequency of respirations, or other aspects of motions associated with breathing. The user interface can also display indicia of the patient's health. The indicia can include an alert informing the patient that it is time to seek medical help or to take medication.

Figure 21:
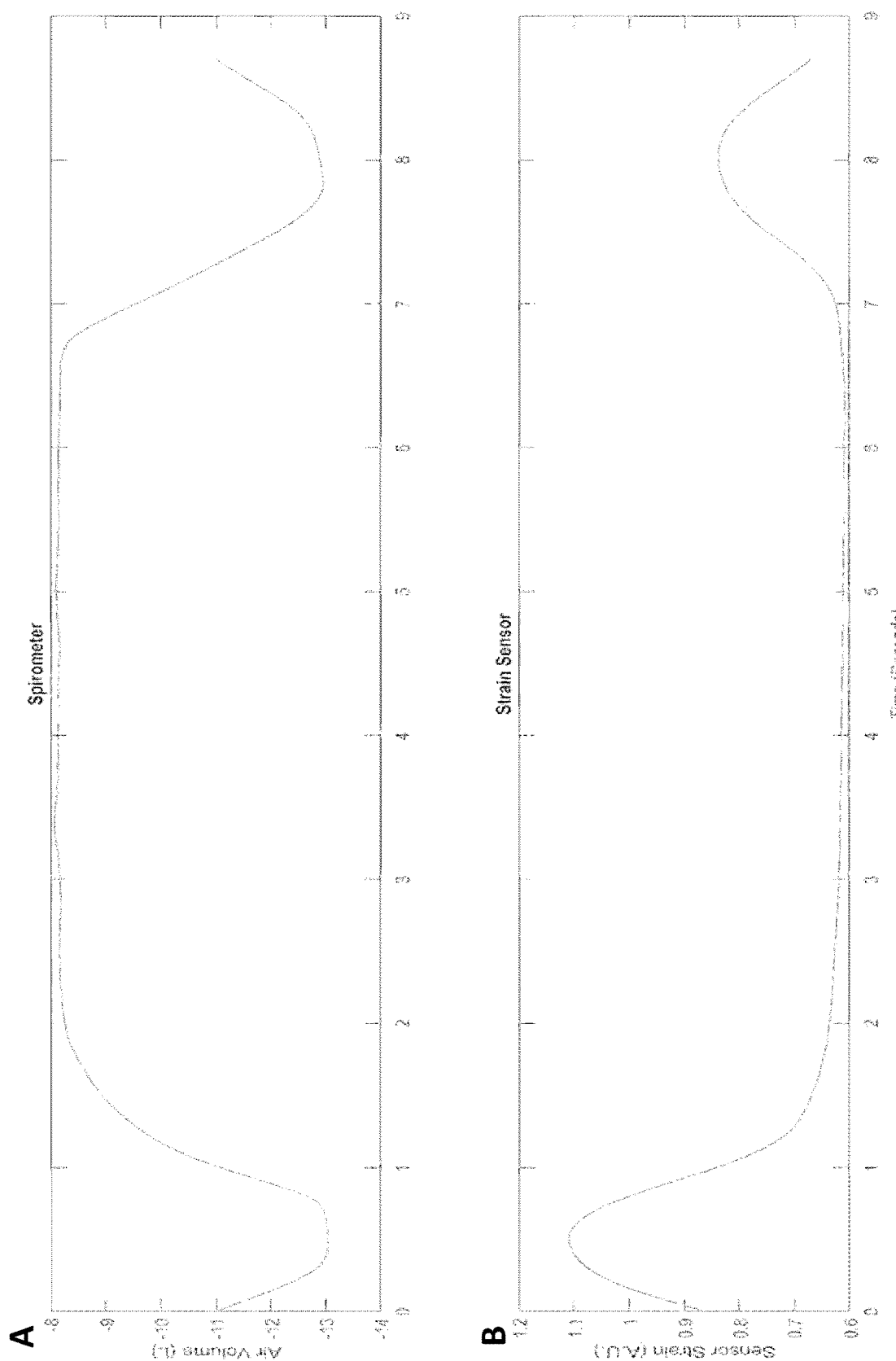
FIG. 21. Enlarged sections of data from FIG. 20 showing the last pulmonary function test (PFT) measurements by (A) spirometer and (B) Asthma Sensing Predictive Intuitive Respiratory E-alert Monitor sensor.
Figure 22:
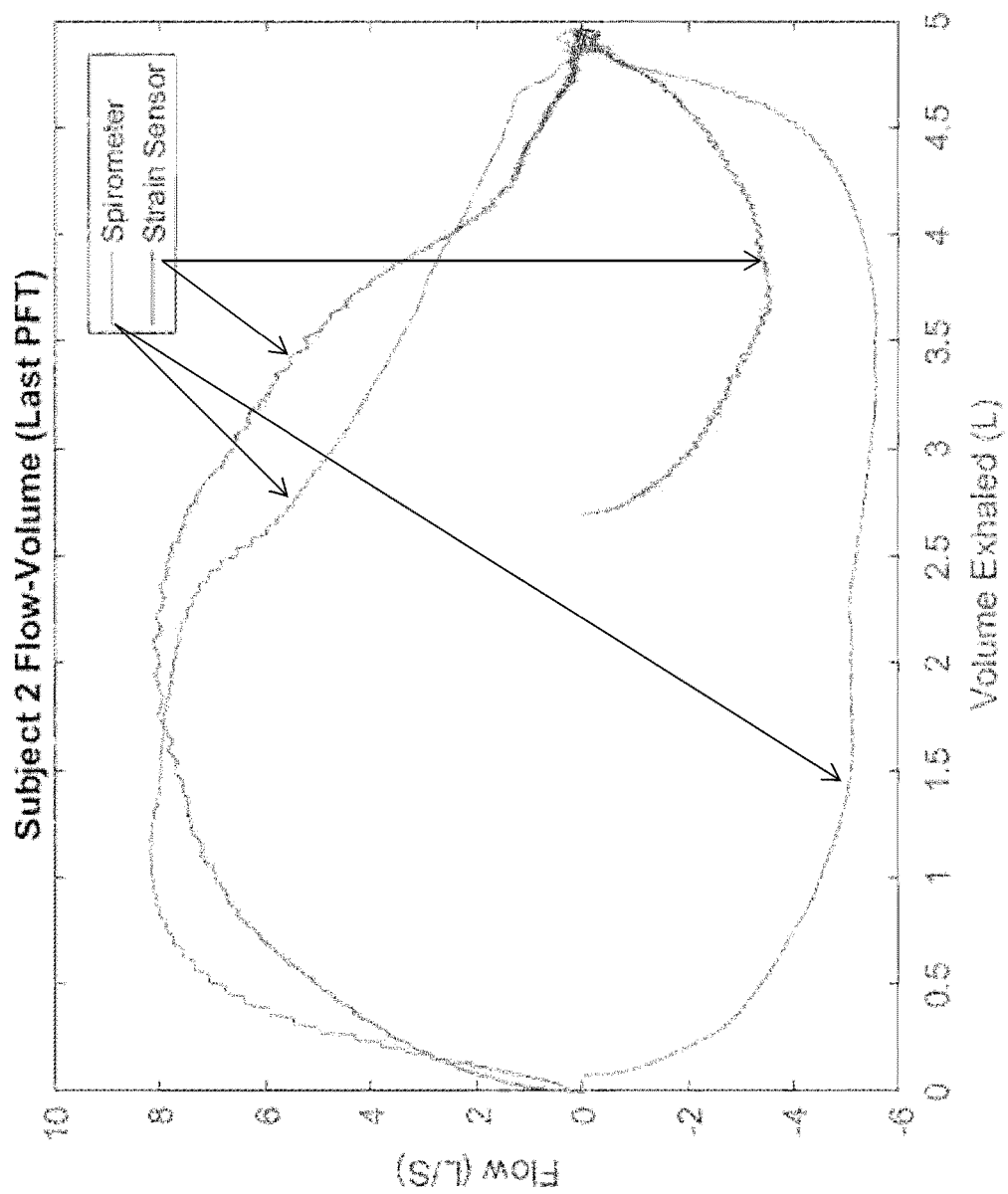
FIG. 22. Comparisons of flow (L/S) to volume exhaled (L), as measured by spirometer and Asthma Sensing Predictive Intuitive Respiratory E-alert Monitor sensor.

The calculator module 54 of the RMS 40 can process received data from the sensor 100 to determine characteristics or indicia corresponding to the patient wearing the sensor 100. The calculator module 54 may implement machine learning algorithms for determining respiratory parameters. The machine learning algorithms may be processor intensive. Accordingly, some of the functionality of the calculator module 54 described herein can be implemented remotely on a remote system 70. The user system 10 can transmit some or all of the received data to the remote system 70 over a network 74. The functionality of the calculator module is described more in detail with respect to FIGS. 21 and 22 below.

Respiration Monitoring System Functional Flow

Figure 3:
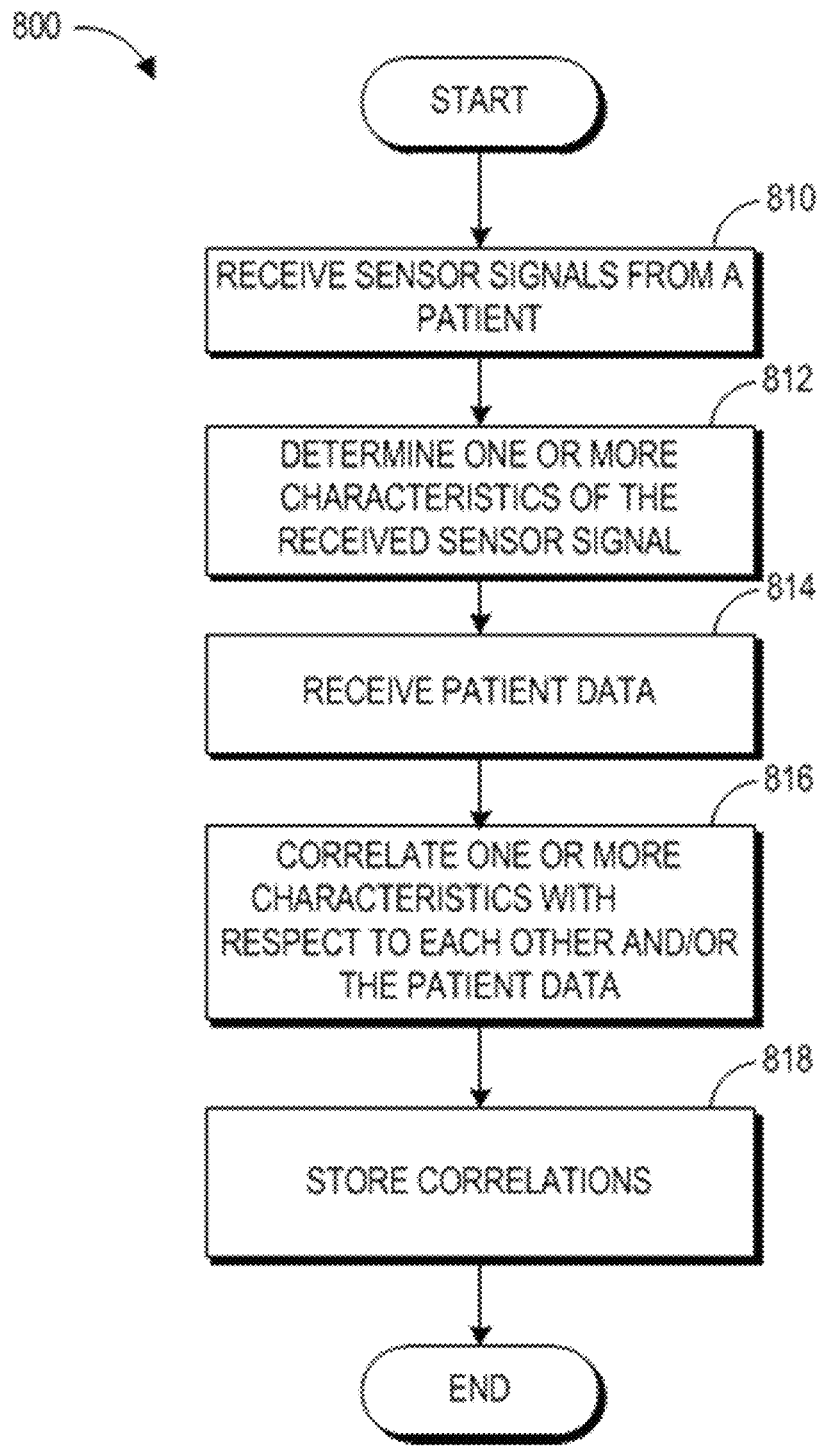
FIG. 3 shows a training set generation process.

FIG. 3 illustrates an embodiment of a method 800 for determining correlations between signal data from the sensor 100 and respiration characteristics. The method 800 can be implemented by any of the systems described herein. In some embodiments, the method 800 is implemented by the RMS 40 described above with respect to FIG. 2.

The process 800 begins at block 810 with receiving sensor signals from a sensor 100 attached to a patient 85. For the purposes of generating a training set, the sensor data can be collected over a period of time and for multiple patients. The period of time can include hours, days, or weeks. In an embodiment, the received sensor data from multiple patients over a period of time is stored in a data repository 76.

At block 812, the calculator module 54 can determine one or more properties of the received sensor signal. For example, the calculator module 54 can determine electrical signatures, including but not limited to the shape, frequency, magnitude, displacement, or width from the received sensor signals.

At block 814, the remote system 70 can receive patient data corresponding to the patients associated with the received signals. Patient data can include patient parameters, such as age of the patient, weight, and the like. Patient data can also include observed data corresponding to the received signal. For example, the received signal can be tagged with events. If a patient undergoes respiratory distress, the corresponding sensor data may be tagged with the event. Additional patient data can include data corresponding to a patient's activity, for example physical exertion or having a meal. Tagging sensor data with the patient data such that the patient events are approximately synchronized in time with the sensor data can be advantageous in some embodiments for determining correlations. Dynamic patient parameter data, such as weight and time course of a dietary or a medicinal regimen, may also be tagged with the corresponding sensor data.

The calculator module 54 can use the patient data such as tagged data or patient parameters to determine relationships or correlations with signal characteristics. FIG. 3, block 816 indicates the correlation one or more characteristics with respect to each other and/or the patient data In one embodiment, the calculator module 54 uses machine learning algorithms to determine correlation between one or more characteristics of the sensor data. Machine learning can evaluate multiple parameters simultaneously without a priori knowledge; therefore, it can discover unexpected relationships to potentially yield better detection. Furthermore, machine learning can provide a singular quantitative index that can summarize the impact of multiple parameters. Machine learning algorithms can be used, for example, to determine respiratory distress based on monitoring of abnormal movement. Machine learning algorithms can include supervised, such as Support Vector Machine (SVM) or unsupervised, such as k-nearest neighbors algorithms. The calculator module 54 can also use decision tree and regressions-based models to determine correlations and predict outcomes.

In one embodiment, the calculator module 54 uses a Support Vector Machine (SVM) algorithm. The calculator module 54 can use the training data to create an optimal model with generalizability. In an embodiment, the calculator module 54 can classify the data points into two groups by creating a decision boundary that separates the two groups. The model can be evaluated by classifying unseen or withheld data. To ensure that over-fitting does not occur and that the classification model has good generalizability to new data, cross validation can be performed by the calculator module 54. Machine learning algorithms can also identify other classifications from the received sensor data.

At block 818, the correlations or models generated by the calculator module 54 can be stored in a data repository 76. The stored correlations can be used for monitoring a respiratory condition and also determining current and future indicators.

Figure 4:
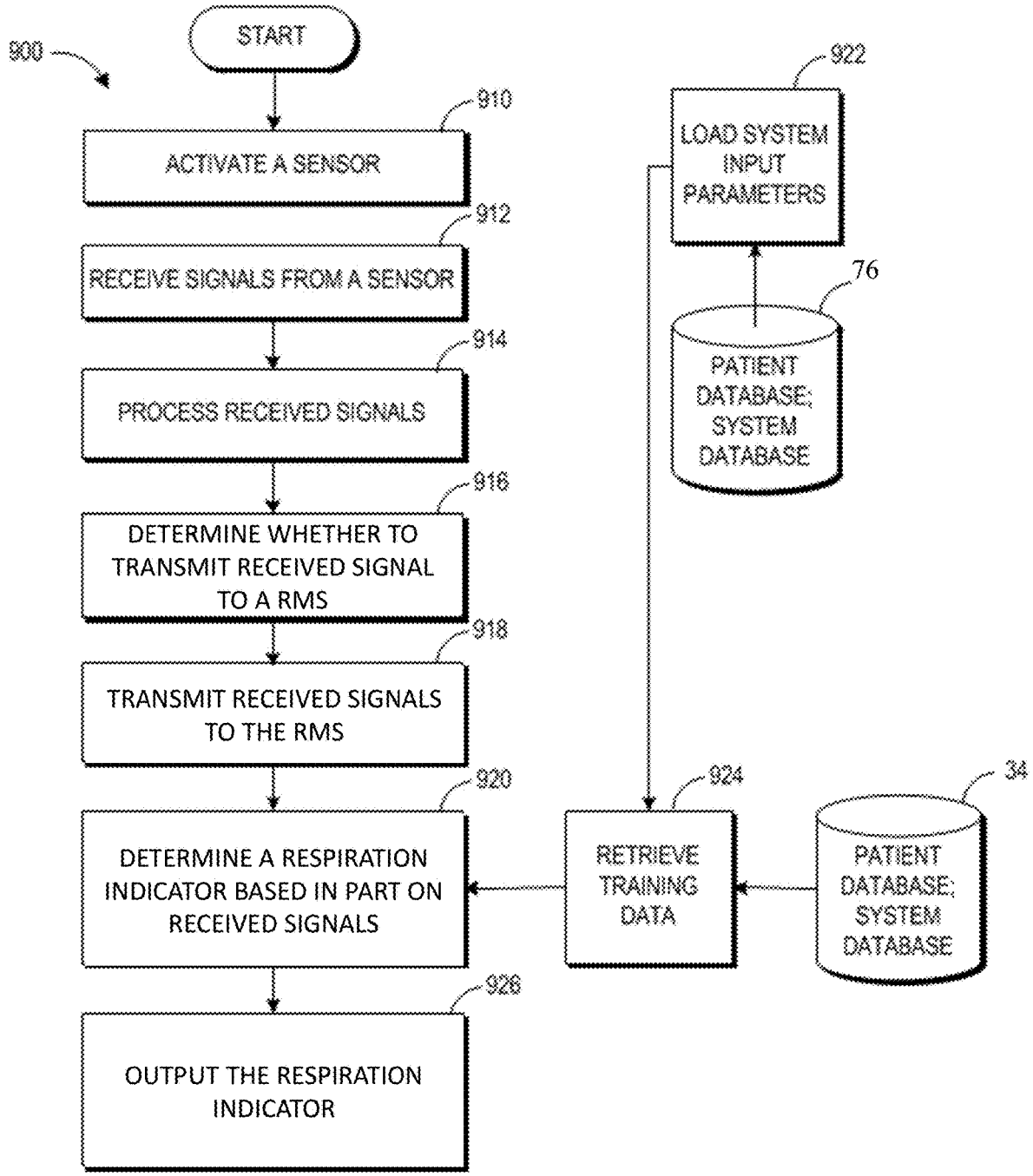
FIG. 4 shows a respiration monitoring system functional flow

FIG. 4 illustrates an embodiment of a process 900 for monitoring a patient using the sensor 100. The process 900 can be implemented by any of the systems described herein. In some embodiments, the process 900 is implemented by the RMS 40 described above with respect to FIG. 2.

The process 900 can begin at block 910 when the processor 24 sends a signal to the measuring circuit 32 to measure a voltage output from a sensor 100 affixed to an expecting mother. The voltage measurement can correspond to a change in resistance or strain of the sensor 100. The processor 24 can receive the measurement signals from the sensor 100 and store it in the memory 26 at block 912. The memory 26 may include a buffer for storing signals, which may be cleared by the processor 24 when the signals are transmitted from the SAM 20.

In some embodiments, the processor 24 can process received signals at block 914 before transmission. Processing can involve extracting a characteristic, such as a frequency, amplitude, or any other signature of the received signals.

At block 916, the processor 24 can determine whether to transmit received signals stored in the memory 26. The determination can be based on the processing of the received signals. For example, the processor 24 can compare the frequency or amplitude extracted from the received signals to a predetermined threshold. As an example, the processor 24 can transmit the received signals when the frequency of the kicks exceeds 10 kicks per 2 hours. In some embodiments, the processor 24 transmits the received signals in response to a request from the user system 10. Further, the processor 24 may also be programmed to transmit the received signals after a predetermined time period, for example, every 30 minutes or 1 hour or 2 hours. The predetermined time period does not need to be a constant and can be a function of the patient data.

At block 918, the radio circuit 22 can transmit the received signals to a user system 10. In an embodiment, signals are transmitted using the Bluetooth protocol. The RMS 40 can determine a respiration indicator based in part on the received signals, shown at block 920. The RMS 40 includes the signal collector module 52 to access the transmitted signals from SAM 20. In some embodiments, the RMS 40 transmits the received signals over a network 74 to the remote system 70 for determination of the respiratory condition indicator or to process at least some aspects of the received signals. The remote system 70 may have access to higher processing and data resources (e.g., Patient Database: System Database 76) as compared to the RMS 40 and SAM 20 for analyzing received signals. Accordingly, it may advantageous in some embodiments to have the processor 72 implement aspects of the calculator module 54, such as the machine learning algorithm, that requires more processor intensive resources.

In an embodiment, the calculator module 54 applies the system parameters, such as models and correlations (as discussed above with respect to FIG. 2I to the received signal data to determine respiratory distress. For example, the calculator module 54 can analyze the received signal data and determine whether it belongs in the class corresponding to respiratory distress or normal movements. The calculator module 54 may generate an alert at block 926. The I/O module 56 can notify the patient by displaying the alert or outputting a sound or a signal (e.g. vibration) at the user system 10. In addition to any alerts, the calculator module 54 may also generate results of the analysis of the received signals. The I/O module 56 can also output a trend chart based on the results.

In some embodiments, the calculator module 54 can also use patient-specific parameters stored in patient data repository 58 or 76 or a patient database/system database 34 to determine respiratory distress. A patient can also input parameters, such as weight or whether the patient has had a meal, using the I/O module 56. The calculator module 54 can use all the available data to determine one or more indicators of respiratory distress.

Crowd Sourcing Applications

Some embodiments relate to crowd-sourced, computer-implemented methods and systems of collecting and transforming portable device data. One embodiment of the invention may be implemented as a system including an electronic device including a sensor configured to collect data, the device configured to automatically collect respiratory data; and a server configured to issue a command to the electronic device to turn on the sensor and transmit data collected by the sensor to the server without any input by the user of the electronic device when a condition is met.

In some embodiments, a server receives data from a plurality of user endpoint devices, such as graphical data, text data, temperature, location and altitude data. The endpoint devices may include a global positioning system (GPS) sensor. The endpoint devices may be smartphones, tablets, digital cameras, laptop or desktop computers or any other electronic device capable of collecting and transmitting this data. Further, any of the user devices may include more than one sensor. In general, each of endpoint devices will include at least one sensor, a processor, memory, a transmitter for transmitting the data to a server, and a receiver for receiving data from the server. The server also includes a processor, a memory, a transmitter for transmitting data to the endpoint devices, and a receiver for receiving data from the endpoint devices.

In some embodiments, the endpoint devices are portable electronic devices that run one of the ANDROID™, iOS™, or BLACKBERRY™ operating systems. An app run by the device performs the functions described herein.

The server may include a complex event modeler and a predictive modeling tool, which analyzes the data received from the devices to determine if the data received from the devices corresponds to a widespread or general respiratory distress event. The server manages and transforms event files and automatically generates notifications, including machine to machine (M2M) notifications, using a computer aided dispatch (CAD) tool, analytic tools, or command and control tools; and/or machine to person (M2P) notifications to a private or public actor to respond to the event by sending an alert(s) to the actor with information about the event derived from the uploaded data. The private or public actor can be an emergency first responder. The action taken by the actor can include dispatching one or more first responder(s), such as an ambulance, or a police vehicle and associated first responder personnel, or causing an alert to be issued, for example.

A complex event modeler is the analytic engine inside the server that allows thousands to millions of data feeds to come in from the endpoint devices, and then alert on pre-defined thresholds.

A predictive modeling tool is the analytic engine inside the server that takes the alerts and data from the complex event modeler and then "predicts" the next likely group of scenarios.

Alerts may be generated by the server or CAD tool based on the data received from the endpoint devices. For example, an operator can set an alert(s) based on certain conditions/groups of conditions being met or exceeded—location, time, key words, air pollution, widespread respiratory distress signals, weather, and/or temperature etc. When the conditions set by the operator are met, the CAD tool automatically generates an alert—machine-to-machine (M2M) or changes a condition on another device.

Notification Module

In some embodiments, the alert and/or notification is automatically transmitted to an endpoint device operated by the entity associated with the alert and/or notification. The alert and/or notification can be transmitted at the time that the alert and/or notification is generated or at some determined time after generation of the alert and/or notification. When received by the endpoint device, the alert and/or notification can cause the device to display the alert and/or notification via the activation of an application on the device (e.g., a browser, a mobile application, etc.). For example, receipt of the alert and/or notification may automatically activate an application on the device, such as a messaging application (e.g., SMS or MMS messaging application), a standalone application (e.g., a data analysis application), or a browser, for example, and display information included in the alert and/or notification. If the device is offline when the alert and/or notification is transmitted, the application may be automatically activated when the device is online such that the alert and/or notification is displayed. As another example, receipt of the alert and/or notification may cause a browser to open and be redirected to a login page so that the entity can log and view the alert and/or notification. Alternatively, the alert and/or notification may include a URL of a webpage (or other online information) associated with the alert and/or notification, such that when the device (e.g., a mobile device) receives the alert, a browser (or other application) is automatically activated and the URL included in the alert and/or notification is accessed via the Internet. An alert may include a map indicating respiratory condition information in connection with a plurality of users. In some embodiments, the map is a heat map, which may be a geographical representation of data in the form of a map or diagram in which data values are represented as colors.

Accordingly, in various embodiments, large amounts of data are automatically and dynamically calculated interactively in response to user inputs, and the calculated data is efficiently and compactly presented to a user by the system. Thus, in some embodiments, the user interfaces described herein are more efficient as compared to previous user interfaces in which data is not dynamically updated and compactly and efficiently presented to the user in response to interactive inputs.

Further, as described herein, the system may be configured and/or designed to generate user interface data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additionally, it has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The various embodiments of interactive and dynamic user interfaces of the present disclosure are the result of significant research, development, improvement, iteration, and testing. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interfaces described herein may provide an optimized display of time-varying report-related information and may enable a user to more quickly access, navigate, assess, and digest such information than previous systems.

In some embodiments, data may be presented in graphical representations, such as visual representations, such as maps, charts and graphs, where appropriate, to allow the user to comfortably review the large amount of data and to take advantage of humans' particularly strong pattern recognition abilities related to visual stimuli. In some embodiments, the system may present aggregate quantities, such as totals, counts, and averages. The system may also utilize the information to interpolate or extrapolate, e.g. forecast, future developments.

Further, the interactive and dynamic user interfaces described herein are enabled by innovations in efficient interactions between the user interfaces and underlying systems and components. For example, disclosed herein are improved methods of receiving user inputs, translation and delivery of those inputs to various system components, automatic and dynamic execution of complex processes in response to the input delivery, automatic interaction among various components and processes of the system, and automatic and dynamic updating of the user interfaces. The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing data storage and processing technology (including, e.g., in memory databases) is limited in various ways (e.g., manual data review is slow, costly, and less detailed; data is too voluminous; etc.), and various embodiments of the disclosure provide significant improvements over such technology. Additionally, various embodiments of the present disclosure are inextricably tied to computer technology. In particular, various embodiments rely on detection of user inputs via graphical user interfaces, calculation of updates to displayed electronic data based on those user inputs, automatic processing of related electronic data, and presentation of the updates to displayed images via interactive graphical user interfaces. Such features and others (e.g., processing and analysis of large amounts of electronic data) are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of electronic data.

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

As used herein, the term "data storage" refers to any computer readable storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. Another example of a data store is a hosted storage environment that includes a collection of physical data storage devices that may be remotely accessible and may be rapidly provisioned as needed (commonly referred to as "cloud" storage).

As used herein, the term "database" refers to any data structure (and/or combinations of multiple data structures) for storing and/or organizing data, including, but not limited to, relational databases (e.g., Oracle databases, MySQL databases, etc.), non-relational databases (e.g., NoSQL databases, etc.), in-memory databases, spreadsheets, as comma separated values (CSV) files, eXtendible markup language (XML) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores.

Machine learning is a subset of artificial intelligence that iteratively learns from data without being explicitly programmed. Thus, a computing device configured to use machine learning techniques to perform an action can learn how to perform the action without being explicitly programmed. Accordingly, the machine learning techniques improve the functionality of the computing device itself because the machine learning techniques allow the computing device to learn, and thereby produce more accurate detections of instances of suspected respiratory distress, without being explicitly programmed. The systems and techniques further permit, among other aspects, improved respiratory distress detection through iterative machine learning.

In general, a human does not use machine learning techniques to perform any actions given that machine learning is a subset of artificial intelligence and humans use human or natural intelligence to perform actions, not artificial intelligence. It would be impractical for a human (or even a group of humans) to identify an instance of suspected respiratory distress using machine learning techniques without the use of a computer. For example, due to the fact that machine learning involves the iterative learning from data, a computing device that uses machine learning techniques to perform an action is not programmed by a human with explicit instructions that cause the action to be performed. Rather, a computing device that uses machine learning techniques to perform an action makes decisions or predictions in the course of performing the action based on a model learned or trained using sample data (e.g., based on a respiratory distress detection model that is trained using one or more sets of training data). Thus, there is not a known set of instructions that a human could simply follow to mimic the respiratory distress detection performed using machine learning techniques.

In some embodiments, features such as "training a respiratory distress detection model using machine learning techniques and one or more sets of training data," "automatically detecting an instance of suspected respiratory distress by an entity using the respiratory distress detection model," and updating the respiratory distress detection model using at least a portion of the feedback data and machine learning techniques for use in detecting a second instance of suspected respiratory distress" can improve the ability of the computer to detect instances of suspected respiratory distress because the features describe a process by which the computer can automatically train a respiration distress detection model to detect instances of suspected respiratory distress without human intervention and can automatically improve the accuracy of the respiratory distress detection model using feedback data.

Example Implementation Details and Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Methods of Monitoring Respiratory Therapy

For patients with respiratory system diseases, such as asthma, COPD, cystic fibrosis and the like, hyper-secretion of mucus is a prominent pathophysiological feature and is often accompanied by impaired mucus transport. This imbalance between mucus transport and secretion results in mucus being retained in the respiratory system. It is useful to monitor respiratory therapy by placing a mobile medical device as disclosed herein in communication with the chest or abdomen of a patient and utilizing output from the mobile medical device to determine if the therapy is being carried out effectively. This enables a user to be made more aware of how well he or she is complying with a prescribed therapy program so that he or she can modify his use of the device accordingly to achieve maximum benefit. The clinician is also able to check patient compliance to identify whether any deterioration in a patient's condition is due to lack of compliance or if alternative treatment is needed.

The respiratory monitors disclosed herein can be used to provide feedback regarding patient compliance with a drug regimen, for example to evaluate drug compliance, e.g., in individuals with asthma or chronic obstructive lung disease, in some cases in specific relation to the use of asthma drugs or COPD medications, which may be administered via inhalers. The respiratory monitors disclosed herein may be used in combination with medication delivery devices, e.g., computerized inhalers, such as the SMARTINHALER™ that contain sensors that can attach to existing inhalers and record when a medication is taken. They are BLUETOOTH®-enabled, so that they can be paired wirelessly with a smart device like a phone or tablet or with a computer to allow data to be transferred from the smart inhaler automatically and can automatically send usage data to a mobile app or PC via BLUETOOTH®. They can also alert users when it's time to take preventative medication and/or report compliance to medical personnel.

Flexible Miniaturized Sensor Apparatuses

A variety of structures can be incorporated into a sensor apparatus to reliably detect a fluctuating signal, such as a detectable change in resistance, for motion detection in a disposable wearable sensor (WO 2015/179320). FIGS. 5-11 illustrate thin film metal strain gauges and FIGS. 12-15 illustrate one-dimensional structures, including nanotubes and nanowires for use as disposable wearable strain gauge sensors.

1. Sensors Having a Metal Film Conductor

Figure 6:
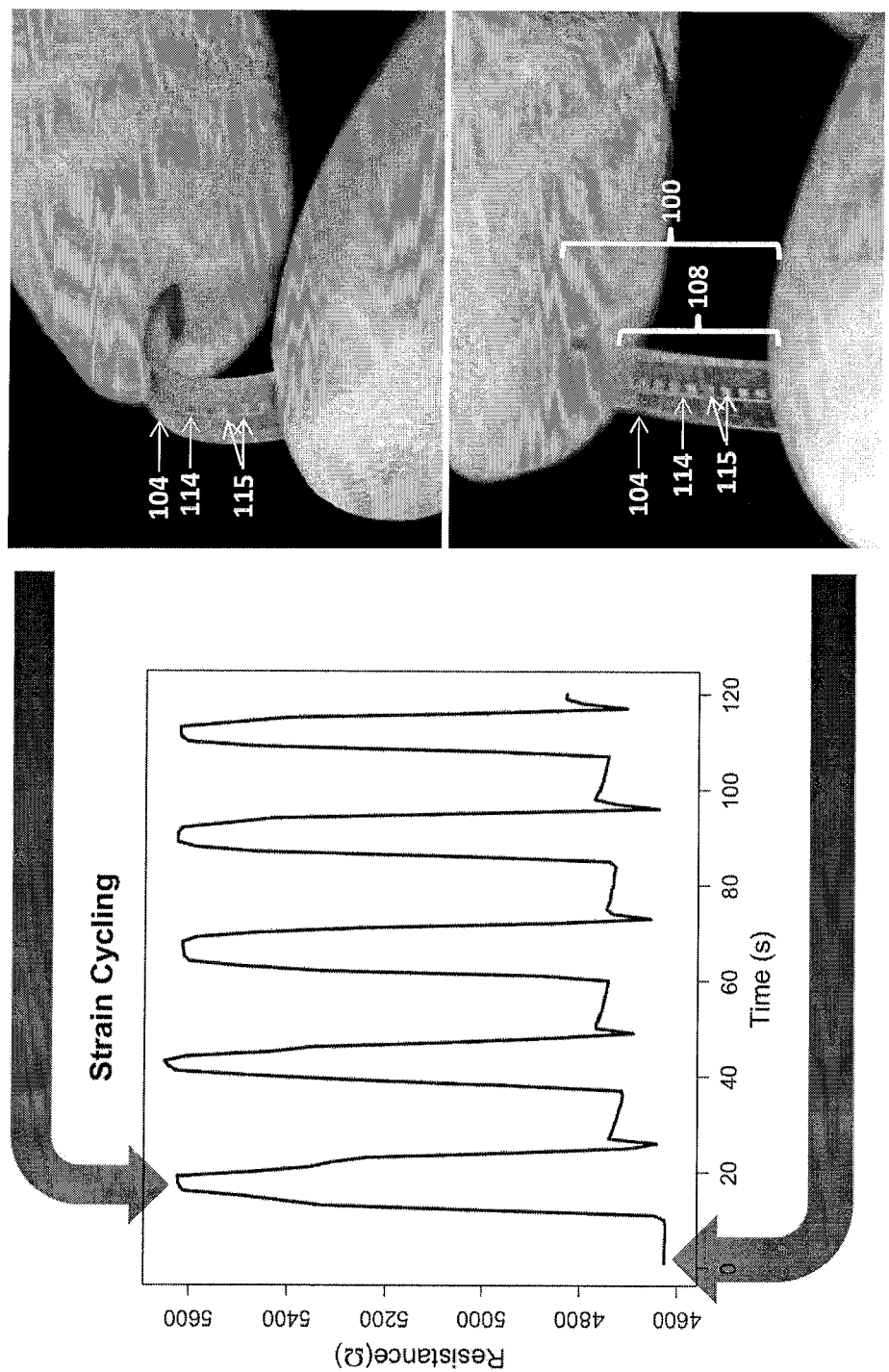
FIG. 6 shows the resistance response of a wrinkled metal film strain gauge. Resistance peaks correspond with maximum strain of 5%. The bottom arrow indicates the initial, unstrained resistance of the wrinkled metal film strain gauge.

In one embodiment, as depicted in FIG. 5, the sensor apparatus 100 includes a flexible substrate 104 and a conductor 108. In the illustrated embodiment, the conductor 108 initially is formed as a thin metal film but thereafter crumpled or wrinkled because the material it is formed upon is shrunk to a fraction of its initial size. A plurality of electrical contacts 110 and 112 are in electrical communication with the conductor 108. The electrical contacts 110, 112 can be disposed at opposite ends of an elongate conductive region 114. In other embodiment, more than two contacts can be provided. For example, FIG. 6 shows one modified embodiment in which a plurality of contacts 115 are disposed along the length of an elongate conductive region 114 on flexible substrate 104. The contacts 115 in this embodiment are disposed to one side of the elongate conductive region and allow connection to other devices at a number of different positions and/or permit a number of different devices to be in contact with the elongate conductive region. For example, any two of the contacts 115 can be used to measure a signal such as current or a change in a property such as resistance at a location along the conductive region 114.

Figure 7:
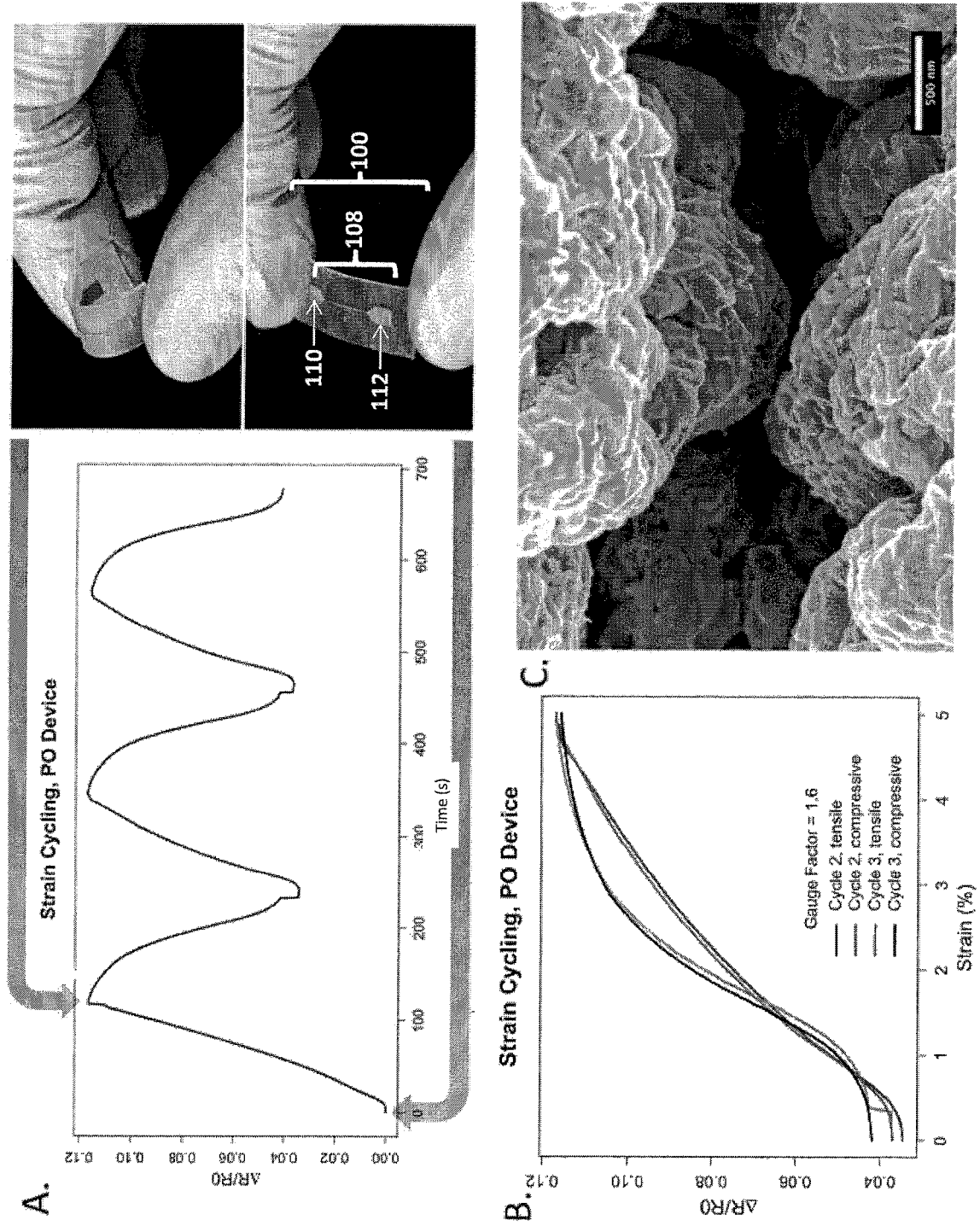
FIG. 7 shows strain cycling of a second embodiment of a wrinkled metal film strain gauge. Panels (A) and (B) show semi-static linear strain cycling. Panel (C) is a top down scanning electron micrograph (SEM) of adjacent wrinkles in contact.

The sensor apparatus 100 is able to undergo very high strain, which induces a detectable change in a signal as illustrated in FIGS. 6 and 7. The signal can be a change in resistance.

One configuration that enables high range of strain is the physical configuration of the film conductor 108. In particular, as shown in FIG. 7(C), at the micron-scale the conductor 108 is not flat but rather is crumpled or wrinkled. This configuration can exhibit secondary folding in some embodiments. Non-shrunk and shrunk electrodes have a linear decrease in resistance across patterned line electrodes of different widths. Measuring electrical resistivity before and after the thermal shrinking process shows a dramatic improvement in electrical conductivity of wrinkled Au thin film electrodes over the non-shrunk, planar Au electrodes. Cross-sections of the wrinkled metal films reveal many tens of micron-scale invaginations in the surface where adjacent wrinkles pack closely enough that they begin to coalesce, referred to as secondary folding. In a flat metal thin film, discontinuities produce a large effect in the resistivity of the film. Without wishing to be bound to any particular theory, we hypothesize that secondary folding in a wrinkled Au thin films creates an increase in electrical contacts, thereby circumventing these discontinuities and reducing the effective resistivity of the wrinkled thin film electrodes.

Moreover, the crumpled configuration of the conductor 108 allows for a great degree of extensibility when subject to strain. The conductor 108 is folded upon itself in the at-rest state and unfolds or unfurls when under strain to an elongate state without being subject to fracture. This mechanical integrity allows the conductor 108 to continue to function even when under strains that are severe for conventional thin film strain gauges.

a. Method of Forming High Strain Film Conductor

Figure 8:
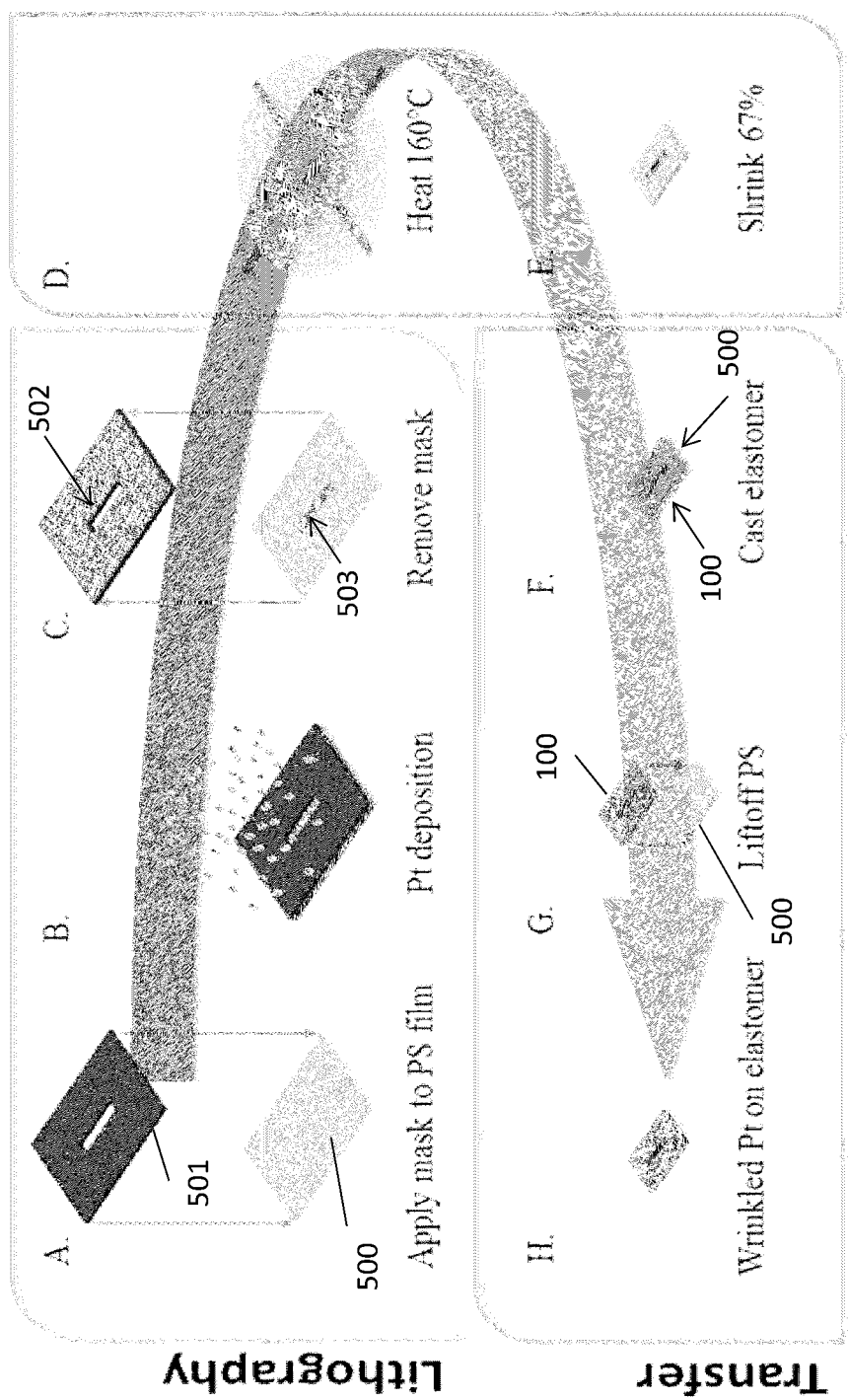
FIG. 8 illustrates a process for making and transferring a wrinkled metal thin film to an elastic material. The process can be separated into 3 sub-processes: Lithography (A-C), Miniaturization (D, E), and Transfer (F-H).

The micron-scale configuration discussed above can be provided by any suitable method. FIG. 8 shows one technique that involves exploiting a heat-shrink material. In FIG. 8, panel (A) the polystyrene shrink film is masked. In panel (B) a metal thin film is deposited. In panel (C), the mask is removed and in panels (D and E) the shrink film is heated to 160° C., shrinking the metal patterned polymer by about 67% by surface area. In panel (F), a flexible polymer, such as ECOFLEX 30™, is spin coated onto the shrunken sample and cured. In panel (G), a series of solvent baths or other separation technique is used to lift off the polystyrene, resulting in the wrinkled metal thin film transferred onto the silicon elastomer (panel H). In some embodiments, a polymeric sheet 500 of suitable heat-shrink characteristics is placed adjacent to a mask 501 configured to block regions of the polymeric sheet 500. This may be followed by a step of depositing a conductive structure 503 on the polymeric sheet 500 at regions exposed through the mask 502. After the conductive structure 503 is formed, the mask 501 can be removed. The process then follows with shrinking the polymeric sheet 500 with the conductive structure 503 patterned on its surface by heating. The metal-patterned polymer may be reduced in size with regard to surface area by 5%, 10%, 15%, 20%, 25%, 30%, 35%, 40%, 45%, 50%, 55%, 60%, 65%, 70%, 75%, 80%, 85%, 90% or 95%. Thereafter, the conductive structure 503 is transferred to a flexible substrate.

The conductive structure 503 can be deposited by any method, for example by air brushing or by electrospray of a material onto a surface. In some embodiments, the conductive structure 503 comprises any conductive metal. In some embodiments, the metal conductive structure is a thin metal film. In some embodiments the metal is selected from the group consisting of Cu, Ag, Au, and Pt. In some embodiments, the polymeric sheet 500 may be a shape-memory (e.g., a shrink-wrap) polyolefin (PO) film. The shrinking step may performed at a temperature of about 100° C., 110° C., 120° C., 130° C., 140° C., 150° C., 160° C., 170° C., 180° C., 190° C., 200° C., 210° C. or 250° C. Among the materials that are well suited for heat-shrink processing is polystyrene.

b. Sensor Assembly Including a High Strain Film Conductor and Flexible Medium

The foregoing method forms a suitable conductive structure for a sensing apparatus. However, many heat shrink materials are more rigid than would be preferred for some applications. For example, it may be desirable to configure the sensing apparatus with as little shape-retaining characteristics as possible. It may be desired to permit the sensing apparatus to drape over a natural structure such as a joint or an expanse of skin. It may be desirable to couple this highly conformal sensing apparatus to a platform that will retain mechanical integrity during continuous use of an hour or more, up to two hours, or even a period of twenty-four hours or more. Thus, it may be desired to transfer the conductive structure to a flexible substrate. The flexible substrate can provide mechanical backing for the highly conformal sensing apparatus while allowing it to retain sufficient flexibility to reliably and repeatedly detect movement.

In one method, it is desired to transfer the conductive structure 503 to an elastomeric polymer. One technique involves cast molding an elastomeric polymer support 504 onto the same surface of a heat-shrunk polymeric sheet 500 upon which the conductive structure 503 is deposited (see FIG. 8, step F). The cast molding can involve preparing the elastomeric material in liquid form and dispensing it onto the surface upon which the conductive structure 503 is deposited. The liquid elastomeric polymer is permitted to solidify. Thereafter, the conductive structure 503 is sandwiched between an elastomeric layer of the support 504 and the heat-shrunk polymeric layer 500. Thereafter, the heat-shrunk polymeric layer 500 optionally is removed (see FIG. 8, step G), leaving the conductive structure 203 on the surface of the elastomeric layer of the support 504.

Metal patterns can be fabricated directly on polydimethylsiloxane (PDMS) by using stencil masks or photolithography; however, there are some limitations to these methods, such as being restricted to patterns with only simple structures, contamination by wet chemicals and cracks because of a large mismatch in the coefficient of thermal expansion of PDMS and that of metals. More importantly, after direct metal patterning on PDMS, high-temperature processes (e.g., annealing) cannot be applied to the sample because of the low melting point of PDMS. Instead of direct-metal patterning on PDMS, it has been reported that metal patterns can be prepared on rigid substrates (e.g., Si or glasswafer); and then the patterns can be transferred to receiver substrates (e.g., PDMS).

For flexible electronics, a strong bond between the metal and the PDMS substrate is very important in order to fabricate a robust and reliable device that is able to endure the stresses induced by the bending of the substrates. If the metal patterns do not bond strongly to the PDMS surface, they can be damaged or lifted off easily by the applied voltage or fluidic pressure. For example, evaporated Au does not adhere to PDMS due to the weak interaction to PDMS.

An adhesion layer is optionally placed between the conductive structure and the elastomeric layer. In some embodiments, Pt is deposited first on a polymeric material, such as polystyrene (see FIG. 8, step B). This may be followed by deposition of a thin layer of Au, which forms metallic bonds with the Pt. Any silane molecule may be used as a surface adhesion molecule. For example, when silicon (e.g., polydimethylsiloxane (PDMS)) is used as the elastomer, the thin film of Au can be covalently bonded to the silicon elastomer using 3-mercaptopropyl) trimethoxysilane (MPTMS) as a molecular adhesive (Byun I. et al. 2013 *J Micromech Microeng* 23(8): 1-10, incorporated herein by reference). Following heat-shrinkage of the polymeric material (see FIG. 8, steps D and E), the gold surface is treated with 3-mercaptopropyl) trimethoxysilane (MPTMS), which functions as a molecular adhesive in bonding the conductive layer to the silicon elastomer. When the wrinkled, conductive layer attached to the elastomer is lifted off of the heat-shrunk polymer, the Pt is exposed.

Several methods to promote adhesion between metal patterns and PDMS are known. The first is to use Ti or Cr as an adhesion interlayer and then activate and hydroxylate the respective surfaces of the metal and PDMS by oxygen plasma or $UV/O_3$ exposure in air. Conformal contact of two hydroxyl (—OH) groups on Ti (5 nm) surface (titanol) and hydroxylated PDMS surface (silanol) by oxygen plasma treatment results in permanent Ti—O—Si bonds. Cr (3 nm) and $SiO_2$ (30 nm) can be deposited on Au electrodes and delivered to PDMS, which is surface activated by exposure to UV/$O_3$, to form Si—O—Si linkages. Similarly, the adhesion can be enhanced between the metal electrodes and the PDMS by thermal curing a prepolymer of PDMS on Au electrodes with Ti interlayer (5 nm). However, using Cr or Ti as an adhesive layer can deteriorate the optical and electrochemical performance of the device, nor are these elements suitable for bio-applications. However, using a molecular adhesive that bonds to both the metal and PDMS may be an alternative to avoid the problems caused by additional metallic interlayers.

For a molecular adhesive, (3-mercaptopropyl) trimethoxysilane (MPTMS), as a self-assembled monolayer (SAM), is versatile because of the different functionality of its two terminal groups. Simultaneously, the three methoxy (—$OCH_3$) functional end groups can bind to oxide surfaces, while the thiol (—SH) functional head group can bind to metals. MPTMS has been used for the transfer of Au films to PDMS. Au patterns treated with MPTMS can bond to PDMS by pouring a PDMS prepolymer onto the Au patterns and subsequent thermal curing or bringing the Au patterns to PDMS whose surface was activated by exposure to UV/$O_3$. Not only Au, but also PDMS can be treated with MPTMS. This PDMS treated with MPTMS can bond with Au patterns by bringing them into contact.

Other alternative polymer elastomers may be used, such as urethane. For other types of polymer elastomers, corresponding adhesion methods are utilized.

The presence of an adhesion layer that adheres the conductive structure to the elastomeric substrate can significantly improve the dynamic range of a sensor. Without wishing to be bound to any particular theory, this may be because the conductive structure is anchored to the elastomeric substrate, allowing it to stretch in response to strain and to retract to its original conformation upon relaxation of the strain. In some embodiments, the dynamic range of a sensor containing an adhesion layer interposed between the conductive structure and the elastomeric layer is 10%, 20%, 30%, 40%, 50%, 60%, 70%, 80%, 90%, 100%, 110%, 120%, 130%, 140%, 150%, 160%, 170%, 180%, 190% or 100% greater than a comparable sensor that lacks an adhesion layer.

Further steps may involve encapsulating the conductive layer. Further steps may involve coupling the conductive layer with other devices, such as may be used to direct current through the conductive layer, to receive current directed through the conductive layer, to store and/or transmit data regarding the resistance or changes in resistance of the conductive layer, to provide one or more signals to the user or patient or for other purposes.

Figure 9:
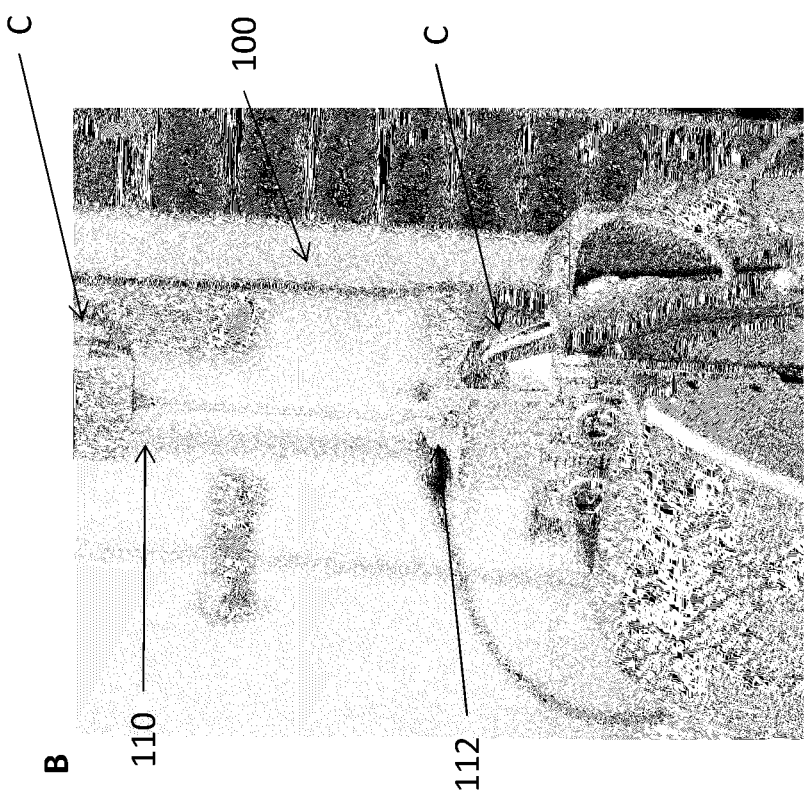
FIG. 9 (A and B) show mechanical integrity tests for an embodiment of a sensor apparatus.
Figure 9:
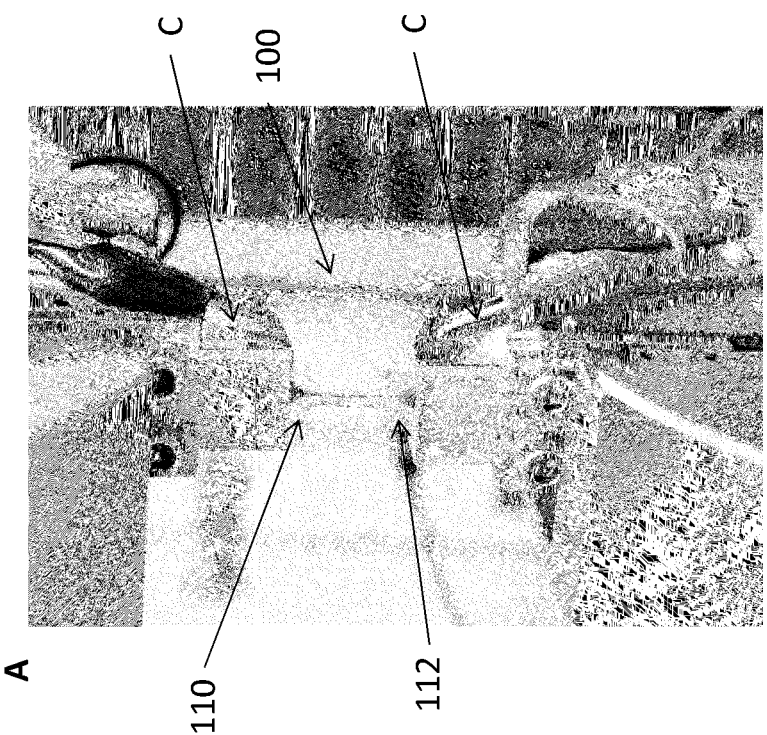

FIG. 9, A and B show mechanical integrity tests for an embodiment of the sensor apparatus 100. The sensor apparatus 200 includes the contacts 110, 112 which can be coupled with electrical conductors C as shown. The ends of the apparatus 100 are illustrated as being coupled with a pull test apparatus. The pull test apparatus pulls the ends of the apparatus 100 away from each other. In the test illustrated, current was caused to flow in a pulled state (panel B) through the sensor apparatus up to a strain of at least 150%. In at least one test a strain of 900% in a pulled state (panel B) was attained to show that the sensor apparatus 100 is able to stretch to a very high degree and still retain its overall structural integrity.

Figure 10:
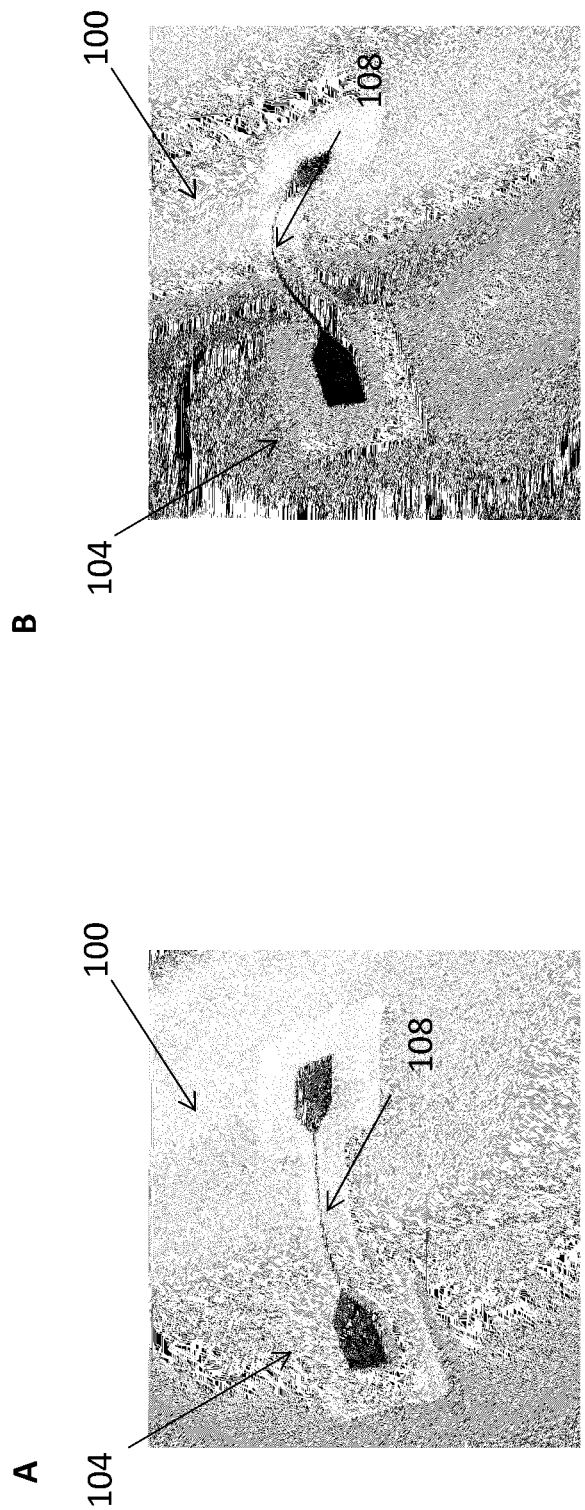
FIG. 10. (A and B) show conformability of an embodiment of a sensor apparatus according to the methods herein.

FIG. 10, A and B show gross mechanical characteristics of the sensor apparatus 100. The sensor apparatus 100 is very flexible and can be draped over a skin structure. The sensor apparatus 100 includes the thin film conductor 108, which is embedded in the flexible substrate 104. The flexible substrate 104 can at least partially encapsulate the thin film conductor 108. Panel A shows a rest state of the sensor apparatus 100 and the skin. Panel B shows a flexed state of the skin. That is, in this test the skin is gathered at a location spaced away from but close to the sensor apparatus 100. The gathering pulls the skin together, causing the ends of the apparatus 100 to move closer together. In this test, the ends move closer together with the skin. The sensor apparatus 100 is flexible so that the skin will return to the state of panel A after being moved to the position of panel B. The flexibility of the flexible substrate 104 is useful in that it helps to maintain the sensitivity of the thin film conductor 108 to the conditions to be sensed.

Figure 11:
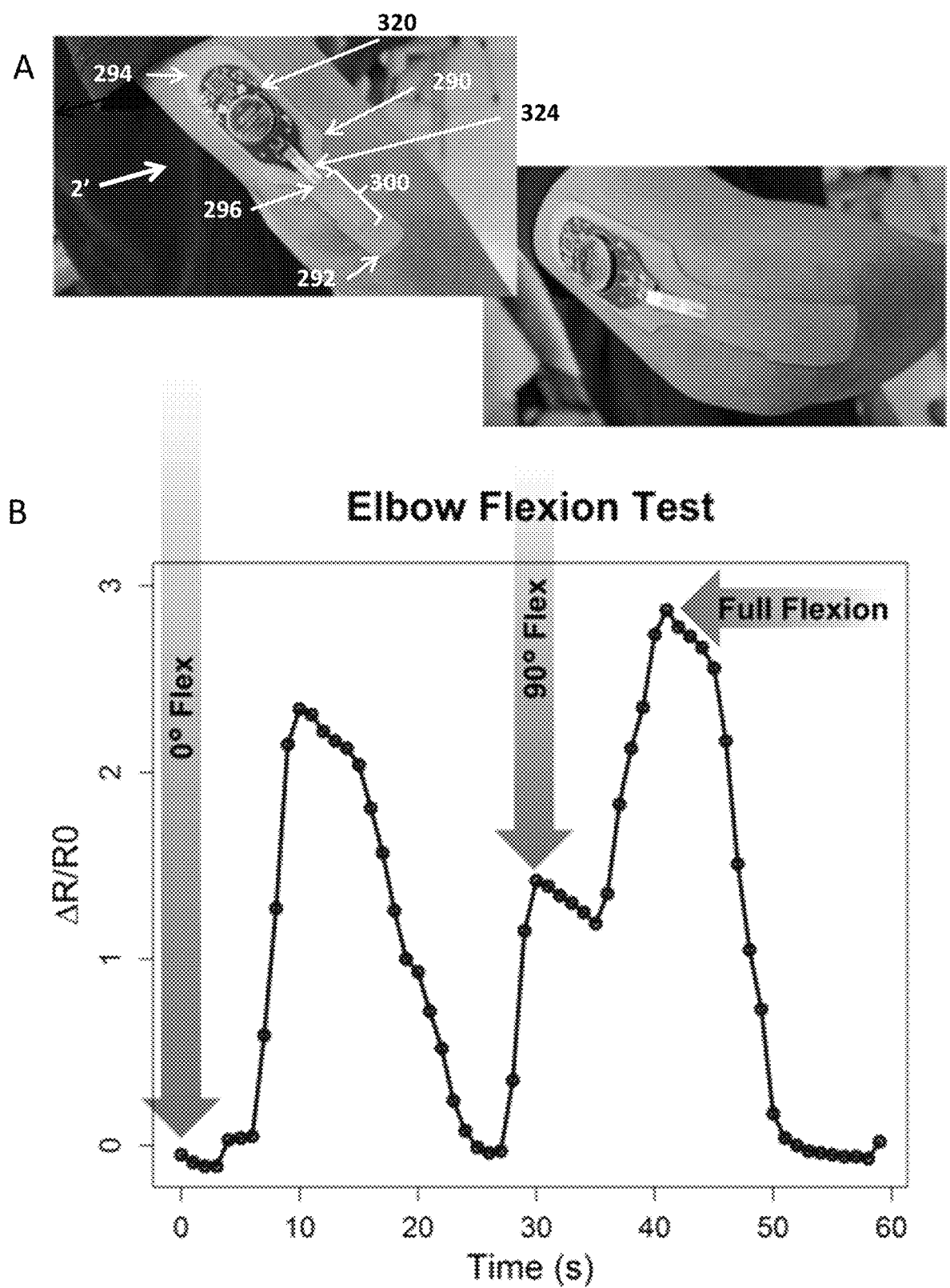
FIG. 11. (A) An assembly including a sensor apparatus and a sensor attachment module and shows an elbow flexion test that demonstrates the performance thereof. (B) Changes in resistance ($\Delta R/Ro$) are measured as a function of elbow flexing.
Figure 12:
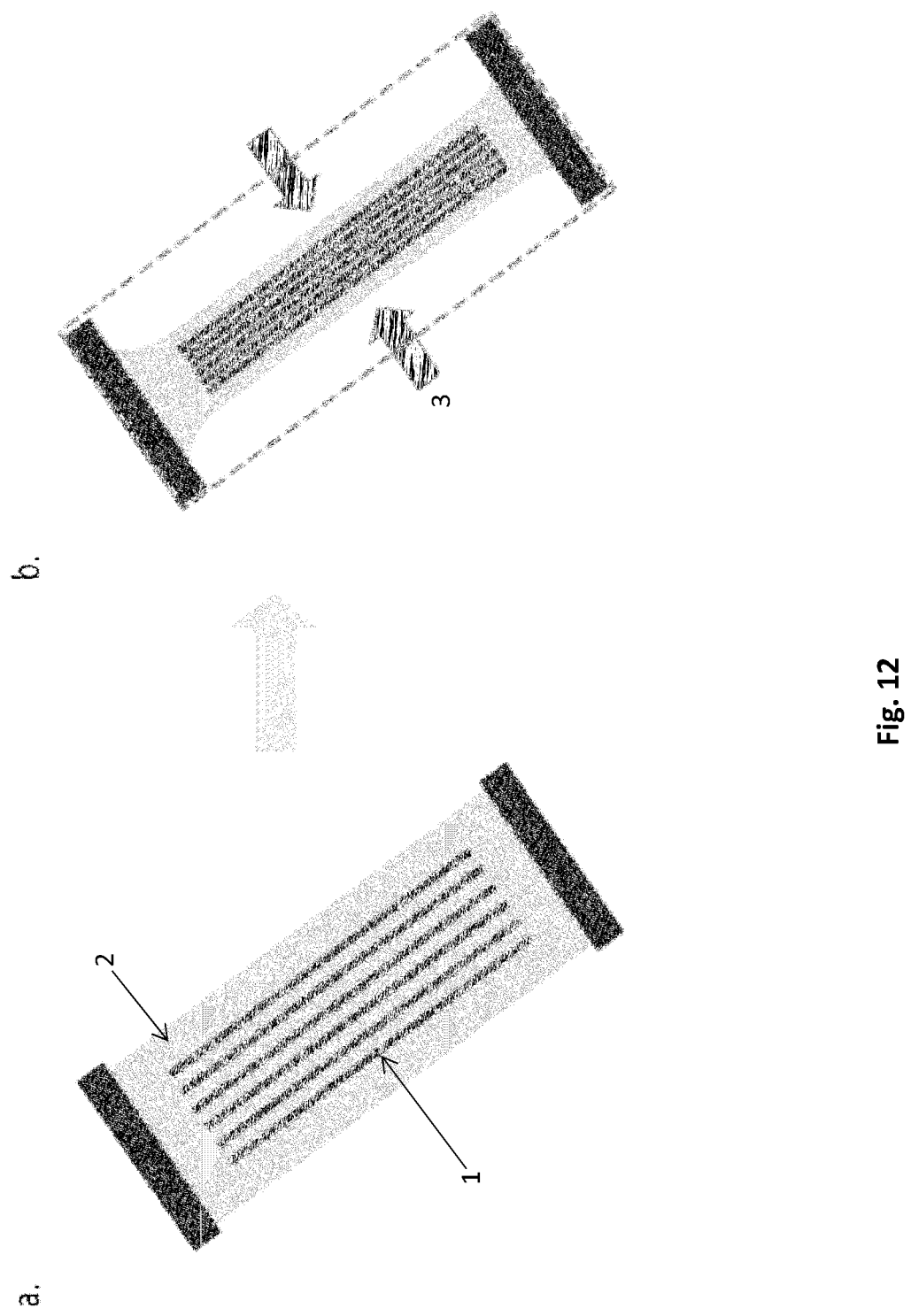
FIG. 12. Schematic of CNT densifying on polyolefin. (a) CNTs (1) on shape memory polymer, e.g., polyolefin (2), before shrinking. (b) CNTs on polyolefin after uniaxial shrinking (3) via heat resulting in densification.

FIG. 11, panel A shows another embodiment of a patient coupled portion and FIG. 11, panel B shows changes in resistance ($\Delta R/Ro$) as a function of strain sensed by a sensor apparatus 300. The patient coupled portion 2' includes a flexible interface 290. The flexible interface 290 includes a first end 292 and a second end 294 disposed on an end of the interface opposite the first end 292. The second end 294 is wider such that it can accommodate a sensor attachment module 320. The sensor attachment module 320 can be disposable or reusable.

The flexible interface 290 preferably includes an aperture 296 disposed along the length thereof between the first end 292 and the second end 294. The aperture 296 is configured to permit a sensor apparatus 300 to be inserted therethrough. When so inserted, the sensor apparatus 300 is located at or adjacent to the first end 292. The sensor apparatus 300 can be entirely disposed under and/or be covered by the expanse of the flexible interface 290. In one embodiment, signals are conveyed from the sensor apparatus 300 to the sensor attachment module 320 by a flex circuit 324 that is extends between the sensor apparatus 300 and the sensor attachment module 320. The flex circuit 324 can include a ribbon cable or assembly of a conductor disposed in a flexible, e.g., polymeric, sheet.

In one embodiment, the sensor apparatus 300, flex circuit 324 and sensor attachment module 320 are provided as an assembly. To apply the patient coupled portion 2', the patient threads the sensor apparatus 300 and the flex circuit 324 through the aperture 296 to dispose the sensor apparatus 300 beneath the flexible interface 290 in direct contact with the user's skin, e.g., directly on the skin of the abdomen just above the belly button. The flexible interface 290 can have an adhesive adapted for coupling with the skin at both the first end 292 and the second end 294. In one embodiment, the first end 292 has a central area in which the sensor apparatus 300 is disposed. The central area can be configured to minimize or reduce the tendency of the flexible interface 290 to create a source of error in the sensor output. For example, if the sensor is a strain gauge the central area can be configured to not have adhesive so that the sensor apparatus 300 can be trapped between the skin of the mother and the flexible interface 290 but not be rigidly adhered to the interface.

In one embodiment, the sensor attachment module 320 is disposable and can be shipped coupled with the flexible interface 290. After use, the sensor attachment module 320 and the flexible interface 290 can be disposed of. In another embodiment, the sensor attachment module 320 is reusable and is configured to be releasably coupled with the flexible interface 290. For example, the sensor attachment module 320 can be coupled and shipped with the flexible interface 290 but can be removed therefrom and reattached by the user to another the flexible interface 290. In one arrangement where the sensor attachment module 320 is reusable, the sensor apparatus 300 can be provided in an assembly with the flex circuit 324. In such arrangement, the flex circuit 324 and the sensor attachment module 320 preferably have connectors enabling the user to electrically couple the flex circuit 324 to the sensor attachment module 320.

Figure 13:
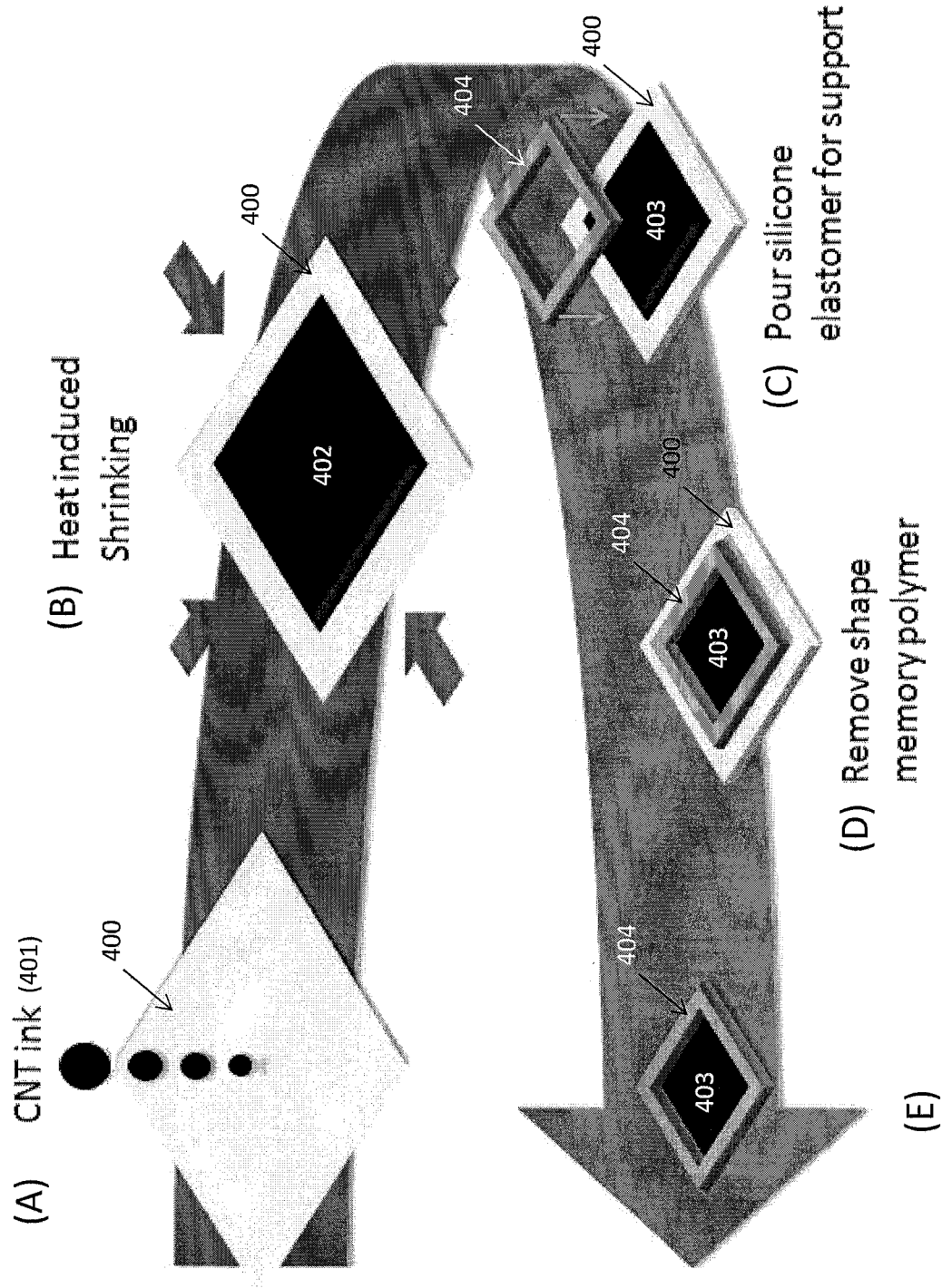
FIG. 13. Process flow for forming a wrinkled carbon nanotube (CNT) thin film. (A) Carbon nanotube ink is deposited on a flexible substrate; (B) Heat induced shrinking of preshrunk layer of CNT, resulting in shrunk CNT thin film; (C) Elastomer poured and cast onto shrunk CNT thin film; (D) Remove flexible substrate from shrunk CNT thin film and elastomer support; (E) shrunk CNT thin film with elastomer support.
Figure 14:
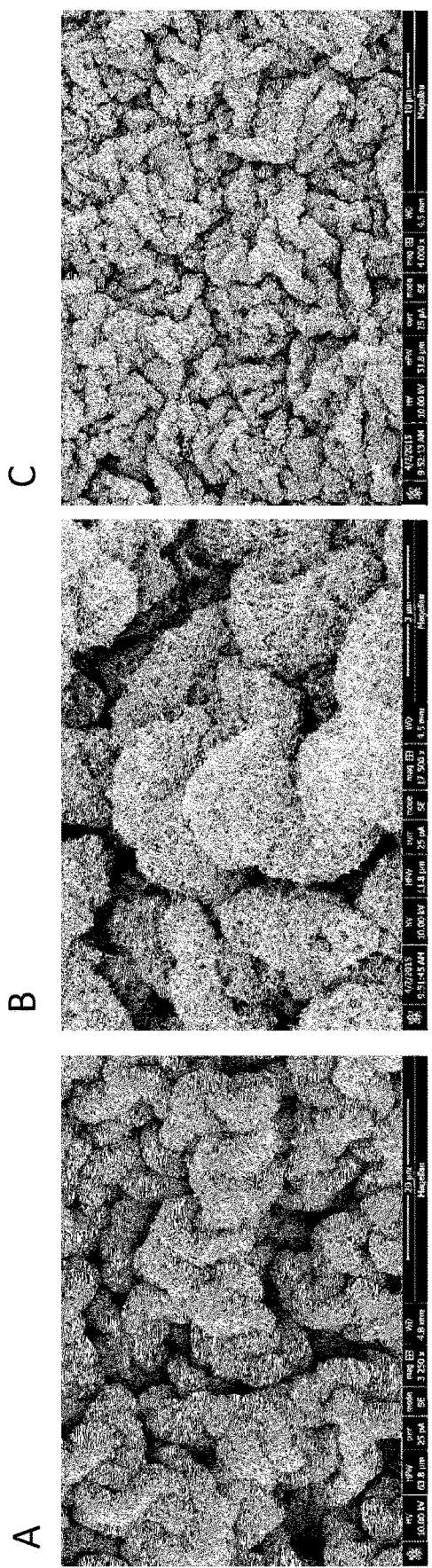
FIG. 14. SEM images of wrinkled CNT thin film at various magnifications. (A) 3,250× magnification; (B) 17,500× magnification; and (C) 4,000× magnification.
Figure 15:
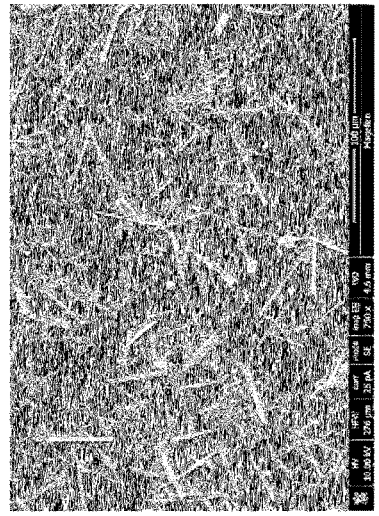
FIG. 15. SEM images of silicon nanowire films before and after shrinking. (A) Before shrinking, 102× magnification; (B) before shrinking, 750× magnification; (C) after shrinking, 103× magnification; (D) after shrinking, 750× magnification.
Figure 15:
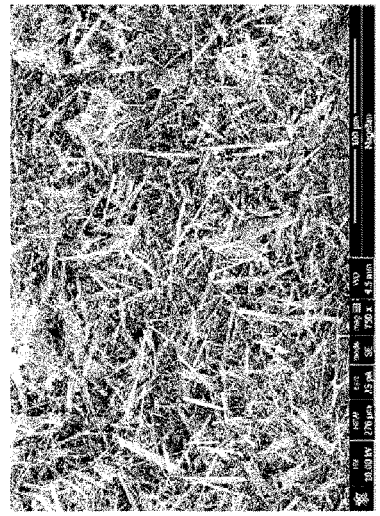
Figure 15:
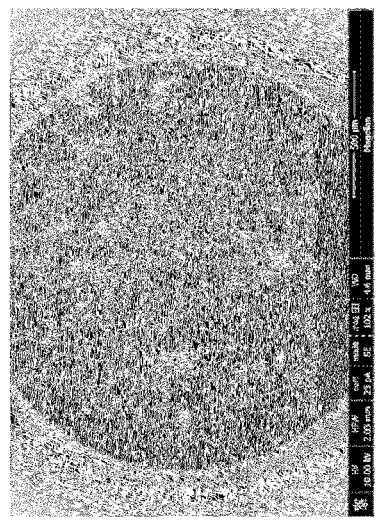
Figure 15:
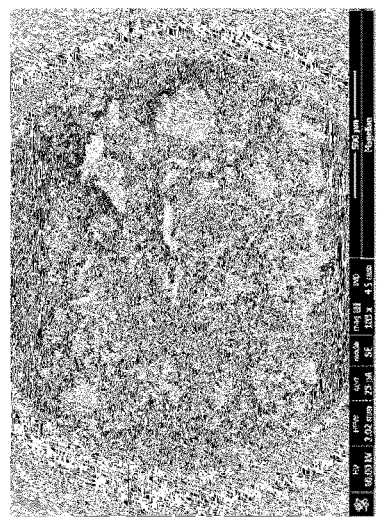

FIG. 13 shows a process flow for forming a wrinkled carbon nanotube (CNT) thin film. In panel A, carbon nanotube ink 401 is deposited on a flexible substrate 400. In panel B, heat induced shrinking of preshrunk layer of CNT 402 results in shrunk CNT thin film 403. In panel C, elastomer 404 is poured and cast onto shrunk CNT thin film 403. In panel D, flexible substrate 400 is removed from shrunk CNT thin film 403 and elastomer support 404. Panel E shows shrunk CNT thin film 403 with elastomer support 404.

2. Sensors Having a One Dimension Nanostructure

In some embodiments the sensor apparatus 100 includes one-dimensional (1D) nanostructures, such as those depicted in FIGS. 12-15. Such apparatus can include one or more of nanotubes, nanofibers, nanowires, and rods. A class of nanostructures includes nanoconductors. A nanostructure is said to be one dimensional, for example, if it much longer in one direction than in other directions perpendicular to the long direction, for example having a diameter on the order of a nanometer (10-9 meters) and a length larger than 10 nm, larger than 50 nm, larger than 80 nm, larger than 90 nm or larger than 100 nm. Nanotubes include carbon nanotubes, for example. A nanowire is a nanostructure, with the diameter of the order of a nanometer (10-9 meters). A nanostructure can be defined as the ratio of the length to width being greater than 1000. Many different types of nanowires exist, including superconducting (e.g., YBCO), metallic (e.g., Ni, Pt, Au), semiconducting (e.g., Si, InP, GaN, etc.), and insulating (e.g., $SiO_2$, $TiO_2$). As disclosed herein, a 1D nanostructure is densified and aligned to produce an effective conductor, which may be configured as a thin film.

Cost-effective technologies disclosed herein provide a process to highly densify and align 1D nanostructures, such as CNTs, to improve its conductivity using shrink technology. In some embodiments, this is done by depositing a thin film of CNTs on the surface of a shape memory polymer, such as polyolefin. Preferably the polymer is a chemically resistant shape memory polymer. The process includes uniaxially, biaxilally, or multiaxially shrinking the polymer by subjecting it to heat. Increasing the density and alignment of CNTs improves the conductivity of the assembly for strain gauge sensors and other applications that use CNTs. Other applications include batteries and chemical sensors.

We demonstrate that biaxial or multiaxially shrinkage of a CNT thin film produces wrinkled structures. As noted above, shrinking of metal films can produce wrinkling in the film. More generally, this wrinkling occurs if stiffness mismatch is provided between a substrate layer and a layer to be wrinkled or crumpled. We have found that a CNT thin film also produces wrinkling. It is believed that the total amount of van der Waals force between each individual CNTs is strong enough to create a stiff thin layer consequently wrinkling after biaxial or multiaxial shrinkage. This wrinkling phenomenon can be produced on shape memory polymers that shrink. We have also shown that the CNT thin film can be transferred onto a soft silicone substrate after removal of the shape memory polymer.

In some embodiments, the thin film of CNTs is shrunk by heating to a temperature of about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., or about 250° C. or a range bounded by any two of the preceding numerical values.

A polyolefin is any of a class of polymers produced from a simple olefin (also called an alkene with the general formula $C_nH_{2n}$) as a monomer. For example, polyethylene is the polyolefin produced by polymerizing the olefin ethylene. An equivalent term is polyalkene.

In some embodiments, the CNTs are dispersed in a solution of an organic solvent, such as chloroform, prior to deposition on a shape memory polymer. Other non-limiting examples of organic solvents include benzene, toluene and phenyl ethyl alcohol or other solvents (Li et al. 2012 "Dispersion of Carbon Nanotubes in Organic Solvents Initiated by Hydrogen Bonding Interactions" AIChE Journal 58: 2997-3002; Dumonteil et al. 2006 "Dispersion of carbon nanotubes using organic solvents" J Nanosci Nanotechnol 6(5): 1315-1318; and Ausman et al. 2000 "Organic Solvent Dispersions of Single-Walled Carbon Nanotubes: Toward Solutions of Pristine Nanotubes" J Phys Chem B 104: 8911-8915).

Densifying CNTs in a sensor application increases the sensitivity of the sensor, proportional to the degree to which a shape memory polymer shrinks. For example, a 95% reduction in area by shrinking on a polyolefin enables a much higher responsiveness. In some embodiments, a stretch senor or a strain gauge device, containing densified CNTs, has a correspondingly lower electrical resistance upon densification of the CNTs. In some embodiments, the resistance of a film upon densification is reduced to about 100 kΩ. In some embodiments, the resistance of a film upon densification is reduced to about 10 kΩ, about 50 kΩ, about 100 kΩ, about 150 kΩ, about 200 kΩ, about 250 kΩ, about 300 kΩ, about 350 kΩ, about 400 kΩ, about 450 kΩ, about 500 kΩ, about 550 kΩ, about 600 kΩ, about 650 kΩ, about 700 kΩ, about 750 kΩ, about 800 kΩ, about 850 kΩ, about 900 kΩ, about 950 kΩ, about 1000 kΩ, about 1100 kΩ, about 1200 kΩ, about 1300 kΩ, about 1400 kΩ or about 1500 kΩ or a range bounded by any two of the preceding numerical values. A low resistance film allows the development of highly sensitive devices that were previously not feasible based on previously existing technologies.

In some embodiments, the density amplification of the CNTs relative to an initial density upon application of the CNTs to a shape memory polymer is an increase of about 100%, about 150%, about 200%, about 250%, about 300%, about 350%, about 400%, about 450%, about 500%, about 550%, about 600%, about 650%, about 700%, about 750%, about 800%, about 850%, about 900%, about 950%, about 1000%, about 1100%, about 1200%, about 1300%, about 1400% or about 1500% or a range bounded by any two of the preceding numerical values.

CNT density can be measured by a light transmittance test. In some embodiments, the CNT density results in light transmittance values of between about 30 to about 90%. In some embodiments the light transmittance is about 30%, about 35%, about 40%, about 45%, about 50%, about 55%, about 60%, about 65%, about 70%, about 75%, about 80%, about 85% or about 90% or a range bounded by any two of the preceding numerical values.

Examples Applications of Wrinkled CNT Structures

1. Flexible Devices

Wrinkled CNT thin films can be incorporated into flexible devices, such as in sensor apparatuses, including strain gauges. As noted above, the CNT thin films can form the sensing component of the sensor apparatus 100. An advantage of using wrinkled films in flexible devices is the ability to stretch out the wrinkles produced from shrinking. Depending on the shape memory polymer used, it is theoretically possible to stretch out to the original, pre-shrinkage dimensions.

Various applications benefit from strain gauges that can undergo large strains and still produce repeatable, predictable outputs. For example, it is desired that such a strain gauge or other sensor apparatuses can be mounted on a flexible substrate and connected to surfaces that are highly curved, mobile and/or repeatedly flexed during the duty cycle of the strain gauge or sensor apparatus. It would be useful for a sensor apparatus herein to be wearable to enable various monitoring of respiration. In some embodiments, the strain gauge or other sensor apparatuses can be mounted on or integrated into an article of clothing, such as a belt, to facilitate use by a subject.

2. Piezoresistive and Capacitive Sensors with Wrinkled CNT Structures

Wrinkled CNT thin films can also be used in the fabrication of piezoresistive and capacitive sensors (Limpomi, D. J.; Vosgueritchian, M.; Tee, B. C-K.; Hellstrom, S. L.; Lee, J. A.; Fox, C. H.; Bao, Z. *Nature Nanotech.* 2011, 6, 788-792, incorporated herein by reference). As such CNT thin films can be used to provide a capacitive sensor for monitoring a respiratory condition and more comprehensively progress of a respiratory condition. Elastic conductors are advantageous components for use in electronic and optoelectronic devices that facilitate human interaction and biofeedback, such as interactive electronics, implantable medical devices and robotic systems with human-like sensing capabilities. The availability of conducting thin films with these properties provides a basis for the development of skin-like sensors that stretch reversibly, sense pressure, bend into hairpin turns, integrate with collapsible, stretchable and mechanically robust displays and solar cells, and also wrap around non-planar and biological surfaces such as skin and organs.

Figure 16:
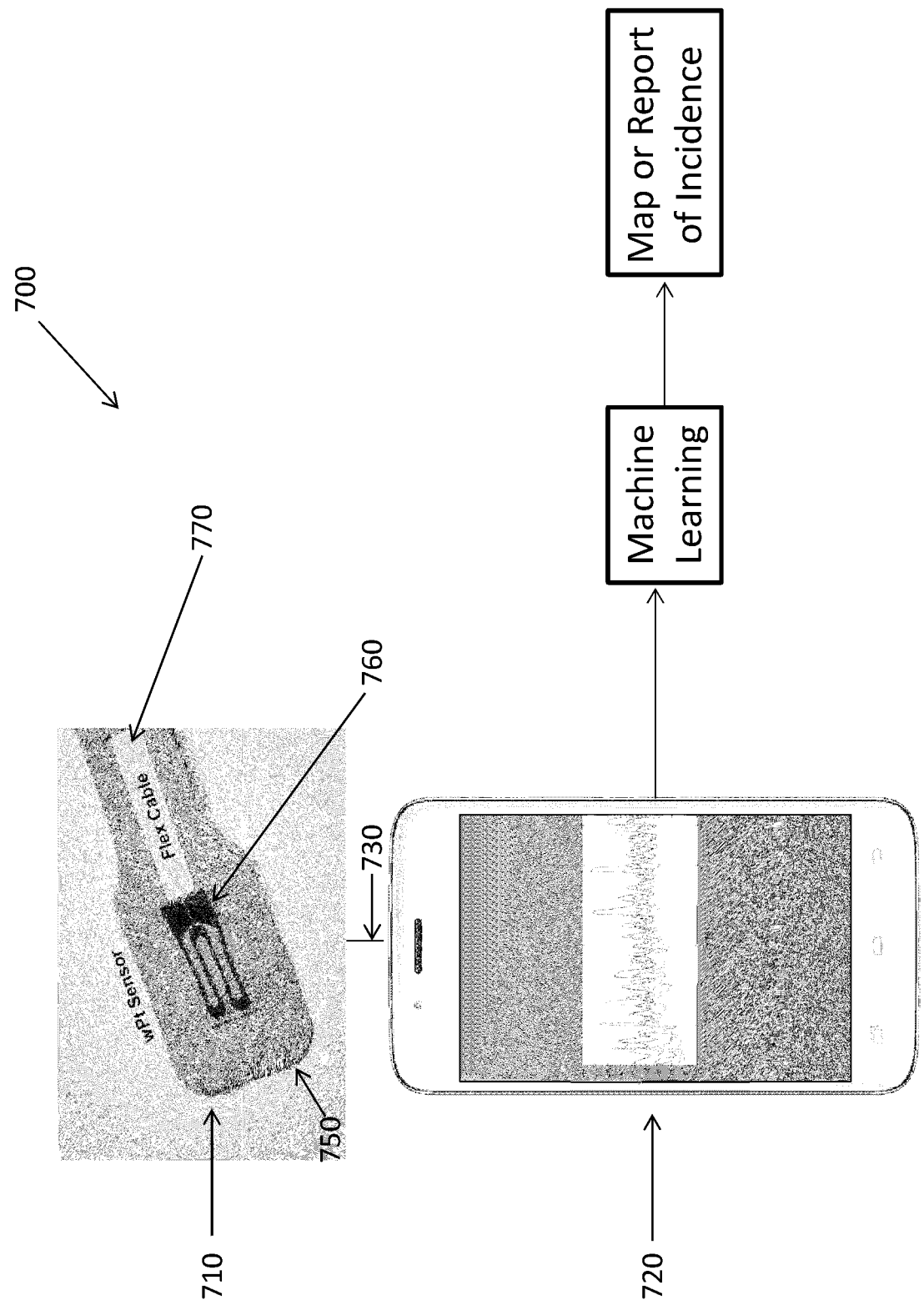
FIG. 16 is a schematic diagram showing a monitor and a flow chart for processing data therefrom.

FIG. 16 shows a predictive respiratory monitor 700 according to one embodiment. The monitor 700 has a sensor 710 and a data processing system 720. The sensor 710 and the data processing system 720 can be in communication with each other by a communication link 730. The communication link 730 can include a direct wired connection, a wireless connection or a combination of wired and wireless connections.

The sensor 710 includes a substrate 750, a conductor 760, and a flex cable 770. The substrate 750 is configured to be coupled with the patient, e.g., adhered to the patients skin. The conductor 760 includes an electrical trace that has a base resistance. The conductor 760 is configured to change resistance upon stretching. More detail about the sensor is set forth in the appendix.

The data processing system 720 can include a processor, which can be combined with other convenient hardware. For example, the data processing system 720 can be configured as a mobile computer such as a smart phone.

The data processing system 720 can receive output from the sensor and can process that output to obtain and communicate accurate measures of relevant patient condition variables, such as lung volume, respiratory rate, and quality and characteristics of respiration.

The data processing system 720 can be configured with machine learning capabilities to not only yield accurate measures but also to improve the performance of the system and to interact with the cloud or with a community of users.

FIG. 16 shows that the data processing system 720 can generate, update and/or display a map or report showing incidence of respiratory abnormalities. The map or report can also be provided to third parties that can use the map as a tool to be informed of areas where abnormal respiration incidents are prevalent.

Figure 17:
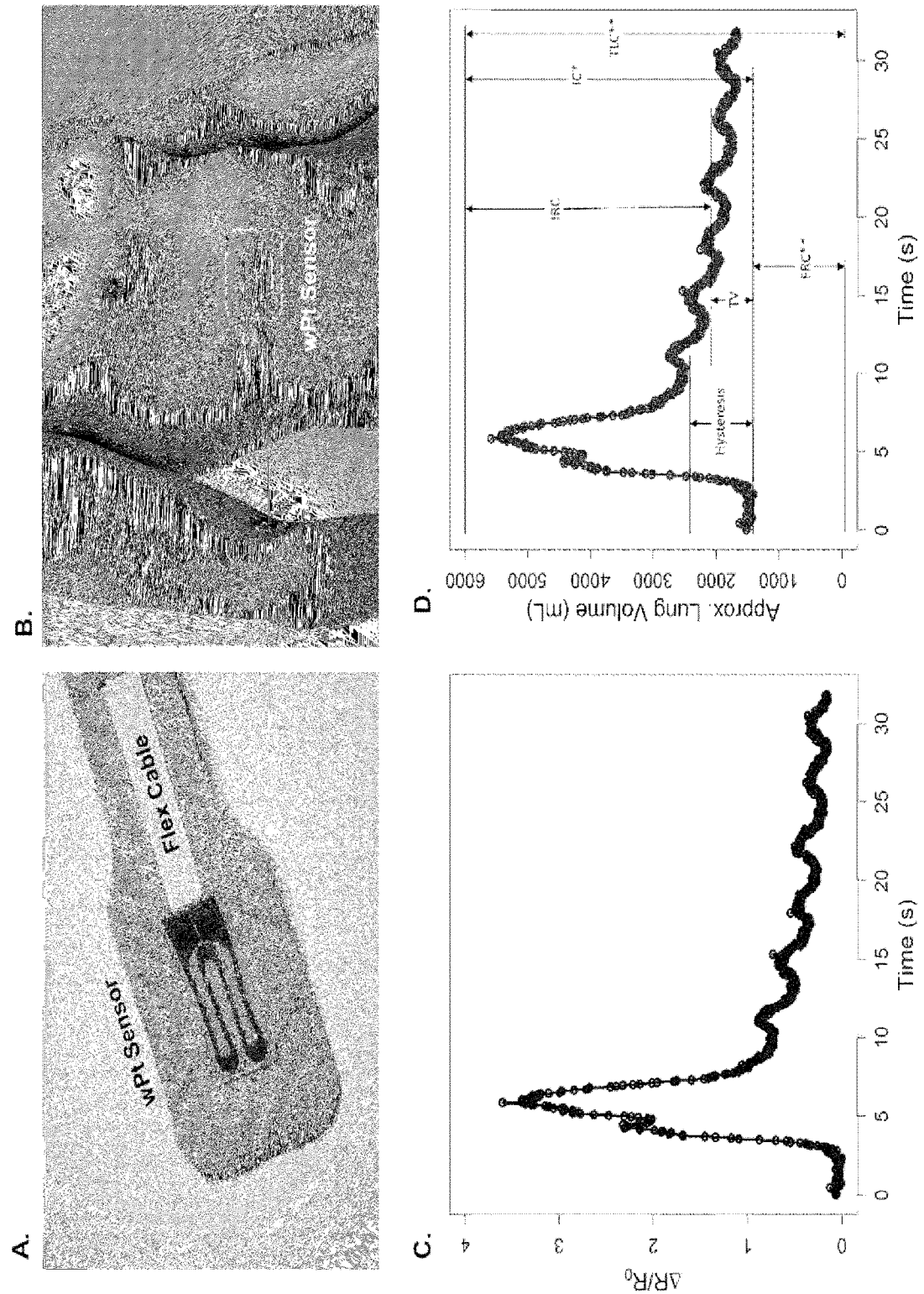
FIG. 17. (a) An embodiment of a sensor for a respiratory monitor, as disclosed herein. (b) The monitor is embedded in a unit configured to be adhered to the skin of a user. (c) A graphical depiction of a signal generated by or obtained from the sensor of (a), with the signal showing a detectable change in resistance compared to steady state at rest resistance. (d) A graphical depiction of an approximation of lung volume over time as derived in a monitor employing the sensor of (a).

FIG. 17 shows more details of the sensor 710. As shown in FIG. 17, (a), the sensor can be integrated into an adhesive strip forming the substrate 750. As shown in FIG. 17, (b), the adhesive strip can be configured to remain on the patient for several hours, a day or more than a day. The sensor 710 is disposable in some embodiment such that it can be discarded frequently, e.g., after showers, baths, or swimming.

The sensor 710 can be mounted in a convenient location on the patient in one method. For example, the sensor 710 can be mounted to the skin of the patient over the lungs. At this location, as the user inhales and the lungs expand, the sensor 710 can be placed under tension and stretched. As the user exhales and the lungs contract, the sensor 110 will return toward an un-stretched state.

FIG. 17, (c) and (d) show signals from the sensor 710 and from the data processing system 720. The signal of $\Delta R/R^0$ in FIG. 17, (c) shows a high peak at around six seconds. This signal is indicative of stretching of the sensor 710. The peak corresponds to a breath being drawn in. FIG. 17, (d) shows a measure of approximate lung capacity. The peak at around six second again corresponds to a breath being drawn in. The output however is in mL of volume as determined by the data processing system 720 base on analyzing the signal from the sensor, for example as depicted in FIG. 17, (c).

Because the sensor 710 is worn by the patient and in generally continuous communication with the data processing system 720 an on-going stream of data that may even be substantially continuous can be obtained and analyzed.

Threshold metrics can be used to detect respiratory conditions. Machine learning can be used to identify noise that may introduce false positive readings or errors into the system. For example, machine learning could be used to factor out of a detection threshold an elevated indication of lung volume that is due to exercise or other respiratory modulation that is not related to an adverse event or condition.

EXAMPLE

ASPIRE: Asthma Sensing Predictive Intuitive Respiratory E-alert Monitor

More than 25 million people (18 million adults and 7 million children) suffer from asthma in the U.S., resulting in over $56 Billion in costs annually [1]. Asthma is the most common chronic disease among children. Annually, in the US alone, asthma results in 10.5 million physician office visits, 1.8 million ER visits, 1.6 million days in the hospital, and over 3,500 deaths. Worldwide, it is estimated that 250,000 people die prematurely each year due to asthma; almost all of these deaths are preventable. Asthma has no cure and its prevalence is growing: it is estimated that by 2025, over 100 million people worldwide will have asthma [2].

The two standard methods that patients can use at home to track asthma patterns are symptom-based journaling and peak flow monitoring [3]. In journaling, patients are expected to record symptoms as well as location and time of incidences; this is currently the best way to monitor how asthma is affecting a patient [4]. Peak flow meters are handheld devices in which patients blow into twice a day and manually record their peak expiratory flow rate. Because of the high variability (sitting or standing results in different recorded flows) and the difficulties associated with ensuring a child exhales maximally, this is not accurate for monitoring young children [5]. In both of these approaches, patients must consistently track symptoms or peak flows for a large period of time (upwards of 40 days) in order to discern any trends. Even then, the trends do not provide accurate predictions of when a patient might encounter an asthma attack [6]. There remains an unmet need for a device or method to automatically detect the on-set of an asthma attack. Patients or caretakers must become proficient in discerning the telltale signs of an ensuing attack, including wheezing, gasping, breathing fast, and shortness of breath. Failure to do so often results in an ER visit. Moreover asthma occurs primarily at night in as much as 75% of asthma patients (typically between 2 am and 4 am) [6].

While there is no cure for asthma, the goal is to keep the disease and its symptoms under control. However, one study showed that as much as 55% of the children who have been diagnosed with asthma had insufficient control [7]. A main factor for insufficient asthma control is poor adherence to inhaled corticosteroids, with typically adherence ranges from only 40-70% [8-10].

Moreover, while inhaled corticosteroids are the preferred long-term treatment to control asthma, these drugs have known significant adverse effects, especially in children [11]. Drug companies are now responsible for drug efficacy. Therefore, understanding personalized dosage response to medication is a vested interest to pharmaceutical companies. Surprisingly, there is currently no way to monitor the effectiveness of medication with the goal to adjust for the minimal effective dosage required.

A recent paper demonstrated that by measuring tidal breathing (unforced, natural breathing) as well within-subject viability using structured light plethysmography (SLP) by monitoring diaphragm can be differentiated [12]. Importantly, this paper demonstrates the feasibility to monitor asthma by simply monitoring changes in diaphragm movement during breathing. However, its limitation is that patients needed to remain stationary to be imaged.

We now provide a basis for being able to continuously and accurately monitor breathing patterns with our unobstrusive, un-tethered small sensors, so that asthmatic children can be effectively monitored. While digitally monitoring diabetes and other chronic conditions has become common place and common sense, the same strategy has not previously been implemented for asthma.

We have developed ultrasensititve piezoresistive strain sensors capable of measuring large mechanical strains of the chest during breathing. The sensors have a form factor of a disposable BANDAID® and can be worn similarly. The strain sensors are comprised of hierarchical wrinkled platinum (wPt) nanostructures embedded into skin-like silicone rubber. These wPT sensors achieve the highest sensitivity over a large and physiologically relevant range of any metal thin film strain sensor [13]. These sensors are extremely conformal to the human body and inexpensive to manufacture. While strain gauges have been around for almost a century, traditional strain gauges do not conform and stretch enough to monitor breathing. While new polymers have been developed to change in resistance upon stretching, the 'gauge factor' (a measure of its sensitivity) of these doped polymers is very low.

Figure 18:
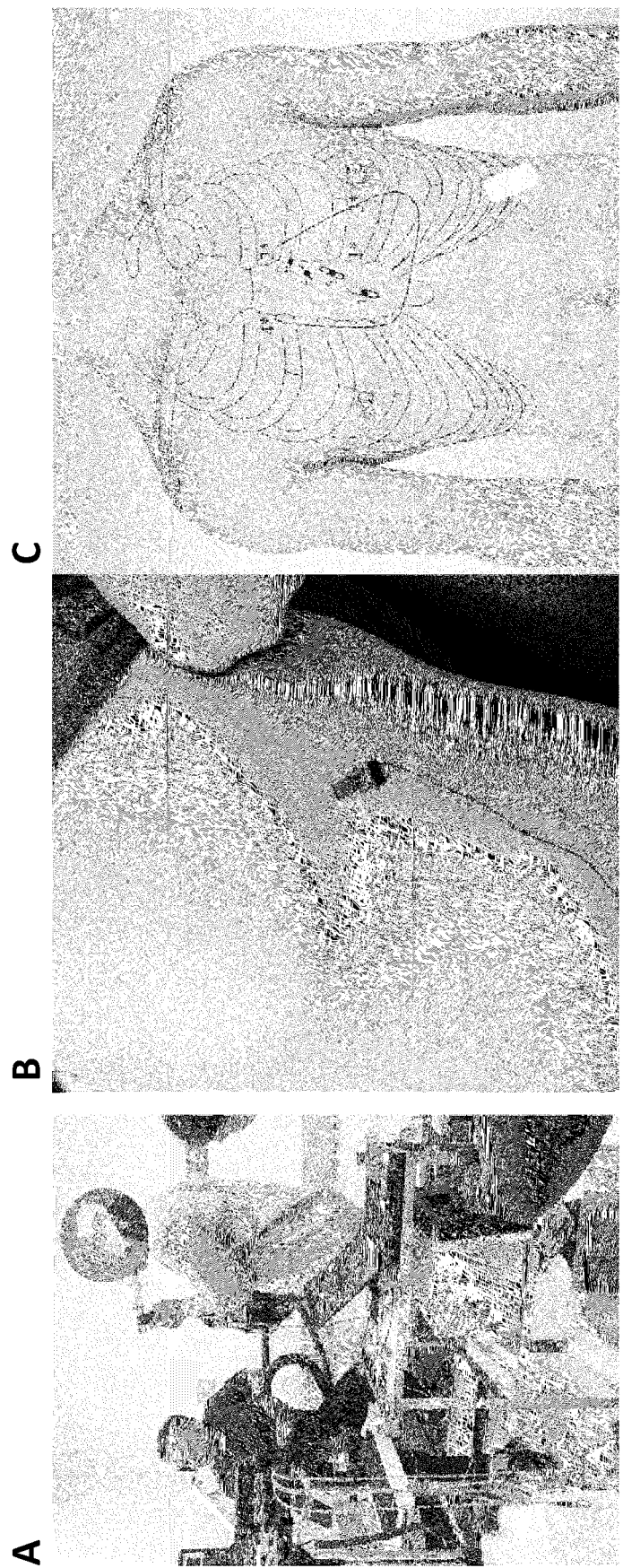
FIG. 18. Human subject trial to correlate wPT sensor data to a medical grade spirometer (CareFusion). (A) Patent undergoing analysis with spirometer. (B) Asthma Sensing Predictive Intuitive Respiratory E-alert Monitor sensor attached to the left side of the thorax. (C) Diagram showing placement of sensor perpendicular to the $10^{th}$ and $11^{th}$ ribs along the anterior axillary line.

We have conducted a human subject trial to correlate our wPT sensor data to the gold standard: a medical grade spirometer (CareFusion) (FIG. 18). Importantly, we have confirmed that we can achieve high correlation with not only breath rate but volume and flow as well (FIG. 19) when compared to spirometry. We can accurately measure tidal breathing as well as pulmonary function tests (PFTs).

Spirometry is a common test offered in a pulmonologist's office used to assess lung function by measuring how much and how quickly air is inhaled and exhaled. It is the standard test to diagnose asthma, chronic obstructive pulmonary disease (COPD) and other breathing conditions. The spirometer costs thousands of dollars and the PFT maneuvers required to assess asthma are not easy for a child with asthma to accomplish (exhaling maximally and as fast as possible).

Our sensors can be used in a continuous respiratory monitor. In combination with our machine learning capabilities, we provide a basis for tracking breathing patterns (breath rate as well as volume) and discernment of subtle changes in breathing patterns, indicative of the onset of an asthma attack. A smartphone app allows the patient/parent to monitor breathing and to visualize wheezing, shortness of breath, and other changes in breathing as well as to save or transmit the data for physician review. In addition, the accelerometer in the phone is used to determine if the person is at rest or if the change in breathing is due to exercise. Finally, we leverage the GPS in the phone to integrate a crowd sourced real-time map of areas with specific asthma-triggers. For example, if a child's asthma is triggered by pollen, it is registered under pollen irritant and the location of other users who are experiencing an onset of an attack due to pollen show up on the map app. This location-specific mapping alerts users in real time to stay away from areas of asthma-triggers.

Figure 19:
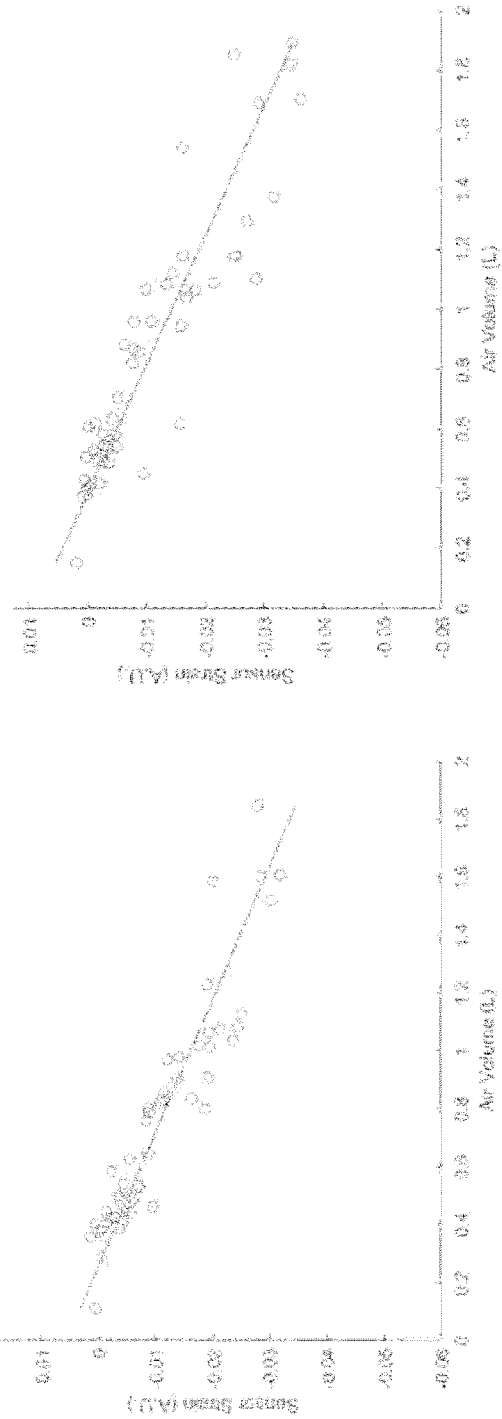
FIG. 19. Sample data correlating spirometer measurements (x axis) with Asthma Sensing Predictive Intuitive Respiratory E-alert Monitor sensor (y axis) for representative female subject (top row) and male subject (bottom row) for both inhalations (left) and exhalations (right). As can be seen from the graphs, we can achieve excellent correlations.
Figure 19:
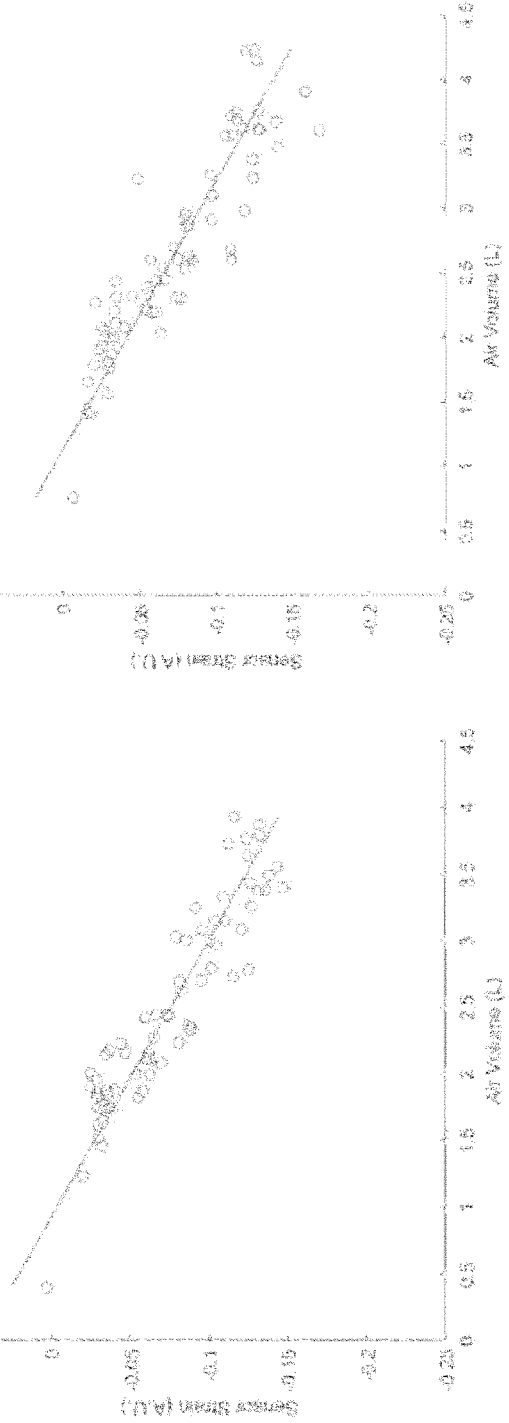
Figure 20:
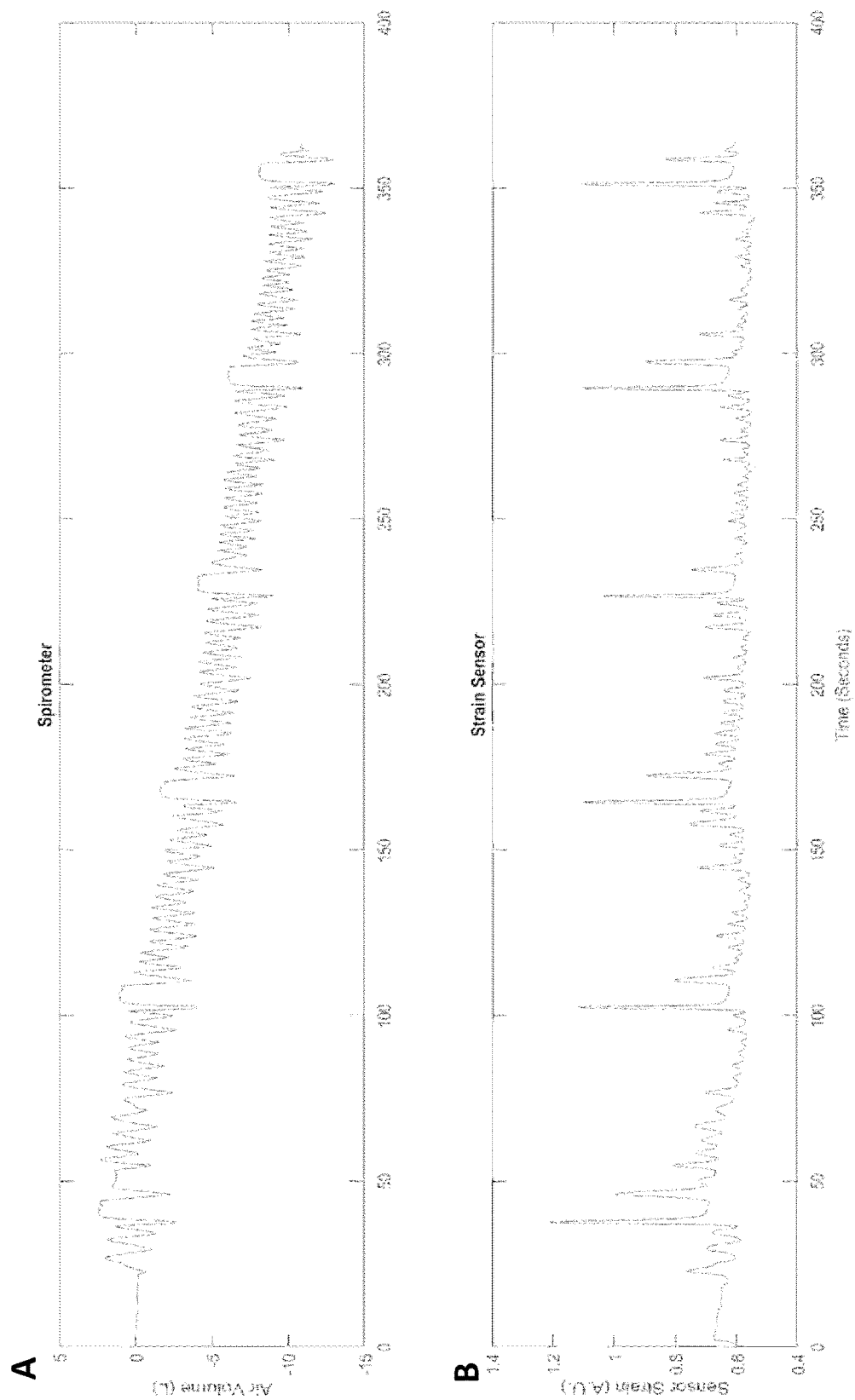
FIG. 20. Example comparison of (A) air volume measurements measured by a spirometer and (B) sensor strain measurements measured by Asthma Sensing Predictive Intuitive Respiratory E-alert Monitor sensor.

We have characterized our sensors and demonstrated that they are quite robust (with cyclic fatigue testing of thousands of cycles) [8]. We have correlated our sensor measurements with spirometry measurements on human test subjects (FIG. 19). The ASPIRE: Asthma Sensing Predictive Intuitive Respiratory E-alert Monitor provides the ability to monitor patients without requiring in-office spirometry.

With respect to sensor fabrication and manufacturability, we have developed processes to scale and reduce the cost of sensors. We have also developed a crowdsourcing app to map allergen/irritants that we can integrate with our sensors. In addition, we have developed a framework for converting multitudes of data streams into actionable insights, based on situation recognition by using an open-source, web-based system called EventShop.

REFERENCES

1. National Heart Lung and Blood Institute, 'What is Asthma?" U.S National Library of Medicine. U.S. National Library of Medicine, n.d. Web. 2 Nov. 2016.
2. World Health Organization. Global surveillance, prevention and control of chronic respiratory diseases: a comprehensive approach, 2007.
3. "Living With Asthma." National Heart, Lung, and Blood Association, National Institute of Health, 4 Aug. 2014. Accessed 1 Nov. 2016.
4. Kamps A W, Roorda R J, Brand P L. Peak flow diaries in childhood asthma are unreliable. Thorax 2001 March; 56(3):180-182
5. Yoos H L, Kitzman H, McMullen A, Henderson C, Sidora K. Symptom monitoring in childhood asthma: a randomized clinical trial comparing peak expiratory flow rate with symptom monitoring. Ann Allergy Asthma Immunol 2002 March; 88(3):283-291.
6. Asthma In-Depth Report, New York Times, www.nytimes.com/health/guides/disease/asthma/print.html 7. Hammer S C, Robroeks C M, van Rij C, Heynens J, Droog R, Jobsis Q, Hendriks H J, Dompeling E: Actual asthma control in a paediatric outpatient clinic population: do patients perceive their actual level of control? Pediatr Allergy Immunol. 2008, 19 (7): 626-633.
8. Vasbinder, E., Janssens, H M, e-Monitoring of Asthma Therapy to Improve Compliance in children using a real-time medication monitoring system (RTMM): the e-MATIC study protocol, BMC Medical Informatics and Decision Making, 2013, 13:38.
9. Drotar D, Bonner M S: Influences on adherence to pediatric asthma treatment: a review of correlates and predictors. J Dev Behav Pediatr. 2009, 30 (6): 574-582.
10. Vasbinder E, Dahhan N, Wolf B, Zoer J, Blankman E, Bosman D, van Dijk L, van den Bemt P: The association of ethnicity with electronically measured adherence to inhaled corticosteroids in children. Eur J Clin Pharmacol. 2012, 69 (3): 683-690.
11. Lipworth, B. J., Systemic Adverse Effects of Inhaled Corticosteroid Therapy A Systematic Review and Meta-analysis, Arch Intern Med. 1999; 159(9):941-955.
12. H Hmeidi et al. Tidal breathing parameters measured using structured light plethysmography in healthy children and those with asthma before and after bronchodilator Physiol Rep. 2017 March; 5(5): e13168.
13. Pegan, J. D., Zhang, J., Chu, M., Nguyen, T., Park, S. J., Paul, A., Kim, J., Bachman, M., Khine, M. Skin-Mountable Stretch Sensor for Wearable Health Monitoring, Nanoscale, 2016, 8, 17295-17303.
14. Zhanf, Z., Zheng, J., Wu, Hao, Wang, W., Wang, B., Liu, H., Development of a Respiratory Inductive Plethysmography Module Supporting Multiple Sensors for Wearable Systems Sensors 2012, 12, 13167-13184.
15. Asthma and Allergen Society: www.aafa.org/page/cost-of-asthma-on-society.aspx.
16. Roman, D. H, Conlee, J. D., The Digital Revolution Comes to US Healthcare, Goldman Sachs Equite Report Jun. 29, 2015.
17. Rosenthal, E. The Soaring Cost of a Simple Breath, New York Times, Oct. 12, 2013.

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A mobile medical device for monitoring a respiratory condition in a subject, the medical device comprising:
a strain sensor comprising a wrinkled metal film that has integrated hierarchal nano- and micro-sized wrinkle structures disposed on a flexible substrate, wherein the strain sensor is configured to be adhered to the skin of a patient, the strain sensor being configured to yield a resistance signal that is modulated by movements of a chest of the subject during respiration, wherein a detectable change in resistance of the sensor occurs upon stretching of the strain sensor; and
an electrical connection that connects the strain sensor to a sensor attachment module (SAM), wherein the SAM comprises:
(a) a measuring circuit configured to receive the resistance signal from the strain sensor, and to measure a change in the resistance signal,
(b) a processor configured to compare one or more characteristics of the change in the resistance signal with a stored threshold criteria and to determine whether the change in the resistance signal is indicative of an adverse respiratory event, and
(c) a transmitter configured to wirelessly transmit data to a respiration monitoring system (RMS),
wherein the processor is configured to control transmission of data by the transmitter to the RMS.

2. The mobile medical device of claim 1, wherein the strain sensor is mounted on or integrated into an article of clothing.

3. The mobile medical device of claim 2, wherein the article of clothing is a belt.

4. The mobile medical device of claim 1, wherein the mobile medical device comprises an electronic device selected from the group consisting of a smartphone, a desktop computer, a laptop computer, a netbook, a tablet computer, a smartwatch, an augmented reality wear, a PDA (personal digital assistants), a server, a digital camera, an e-book reader, a video game platform, a television set-top box (or a television with computing capability), a kiosk, and a combination thereof.

5. The mobile medical device according to claim 1, wherein the mobile electronic device comprises a crowd sourcing application configured to receive data from the sensor attachment module, to transmit data to a server and to receive data from the server.

6. The mobile medical device according to claim 1, wherein the crowd sourcing application is configured to permit a user to manually tag an event or to enter descriptive data regarding an event.

7. A respiration monitoring system (RMS) comprising:
(a) a plurality of mobile medical devices according to claim 1, and
(b) a server for integrating data collected by the plurality of medical devices, the server comprising:
a receiver configured to receive data transmitted from the plurality of mobile medical devices, the received data being collected and processed by the strain sensors and processors of the plurality of mobile electronic devices;
an analytic engine configured to integrate data received from the plurality of mobile medical devices to create or update a map indicating respiratory condition information in connection with a plurality of users; and
a transmitter configured to transmit the map to the plurality of mobile medical devices of the plurality of users, wherein the map indicates a respiratory condition to the plurality of users of the mobile medical devices.

8. The respiration monitoring system (RMS) according to claim 7, wherein the map is a heat map.

9. The respiration monitoring system (RMS) of claim 7, wherein the server comprises a machine learning module to detect an adverse regional respiratory event.

10. The respiration monitoring system (RMS) of claim 7, wherein the machine learning module is configured to detect an asthmatic event.

11. The respiration monitoring system (RMS) of claim 7, wherein the server is configured to:
train a respiratory distress detection model using machine learning techniques and one or more sets of training data,
automatically detect an instance of suspected respiratory distress by an entity using the respiratory distress detection model, and
updating the respiratory distress detection model using at least a portion of the automatically detected instance of suspected respiratory distress by the entity and machine learning techniques for use in detecting a second instance of suspected respiratory distress.

12. The respiration monitoring system (RMS) according to claim 7, wherein the server is further configured to analyze the data collected from the mobile electronic devices to determine a further event or a next likely scenario.

13. The respiration monitoring system (RMS) of claim 7, further comprising a database, the server being in communication with the database to store the indication of the adverse respiratory event.

14. The respiration monitoring system (RMS) of claim 7, wherein the respiration monitoring system is configured to provide to one or more user display devices a report indicating a geographic location of one or more adverse respiratory events.

15. A method of assessing lung function and/or of monitoring a respiratory therapy in a subject comprising:
placing the mobile medical device according to claim 1 in communication with the chest or abdomen of the subject, and
utilizing data output from the mobile medical device to assess lung function and/or to determine if the respiratory therapy is being carried out effectively.

* * * * *